United States Patent
Gerion et al.

(10) Patent No.: US 10,928,319 B2
(45) Date of Patent: Feb. 23, 2021

(54) DIGITAL LSPR FOR ENHANCED ASSAY SENSITIVITY

(71) Applicant: LamdaGen Corporation, Menlo Park, CA (US)

(72) Inventors: Daniele Gerion, Oakland, CA (US); Randolph Storer, Hillsborough, CA (US)

(73) Assignee: LamdaGen Corporation, Menlo Park, CA (US)

( * ) Notice: Subject to any disclaimer, the term of this patent is extended or adjusted under 35 U.S.C. 154(b) by 0 days.

(21) Appl. No.: 16/007,559

(22) Filed: Jun. 13, 2018

(65) Prior Publication Data

US 2019/0017105 A1 Jan. 17, 2019

Related U.S. Application Data

(63) Continuation of application No. 14/632,753, filed on Feb. 26, 2015, now abandoned.

(60) Provisional application No. 61/966,576, filed on Feb. 26, 2014, provisional application No. 62/108,979, filed on Jan. 28, 2015.

(51) Int. Cl.
| | | |
|---|---|---|
| *G01N 21/552* | (2014.01) | |
| *C12Q 1/6837* | (2018.01) | |
| *C12Q 1/6825* | (2018.01) | |
| *G01N 33/543* | (2006.01) | |

(52) U.S. Cl.
CPC ......... *G01N 21/554* (2013.01); *C12Q 1/6825* (2013.01); *C12Q 1/6837* (2013.01); *G01N 33/54373* (2013.01)

(58) Field of Classification Search
None
See application file for complete search history.

(56) References Cited

U.S. PATENT DOCUMENTS

| | | |
|---|---|---|
| 6,331,276 B1 | 12/2001 | Takei et al. |
| 8,426,152 B2 | 4/2013 | Gerion et al. |
| 8,879,065 B1 | 11/2014 | Lin et al. |
| 2003/0129618 A1 | 7/2003 | Moronne et al. |

(Continued)

FOREIGN PATENT DOCUMENTS

| | | |
|---|---|---|
| CN | 1460859 A | 12/2003 |
| CN | 1664560 A | 9/2005 |

(Continued)

OTHER PUBLICATIONS

Chen, et al. Plasmon-enhanced colorimetric ELISA with single molecule sensitivity. Nano Lett. 2011, 11, pp. 1826-1830.

(Continued)

*Primary Examiner* — Melanie Brown
(74) *Attorney, Agent, or Firm* — Patterson + Sheridan, LLP

(57) ABSTRACT

Systems, methods, and devices related to detecting a presence of an analyte and/or determining a concentration of analytes are provided. An analyte may be provided on an LSPR-active surface. The LSPR-active surface may comprise sensitivity enhancing labels. The analyte may induce a local change near the LSPR-active surface. The LSPR-active surface may be imaged with an imaging device for images before, during, or after a reaction takes place. Local regions of interest within the images may be analyzed to detect the local changes.

18 Claims, 10 Drawing Sheets

(56) References Cited

U.S. PATENT DOCUMENTS

| | | | |
|---|---|---|---|
| 2004/0078219 A1* | 4/2004 | Kaylor | G06F 19/3418 |
| | | | 705/2 |
| 2004/0126008 A1 | 7/2004 | Chapoulaud et al. | |
| 2005/0100976 A1 | 5/2005 | Bieniarz et al. | |
| 2006/0088445 A1 | 4/2006 | Lewis et al. | |
| 2007/0171408 A1* | 7/2007 | Wang | G01J 3/021 |
| | | | 356/304 |
| 2008/0166036 A1* | 7/2008 | Bloom | G01N 21/6428 |
| | | | 382/133 |
| 2008/0213814 A1 | 9/2008 | Gerion et al. | |
| 2011/0014724 A1 | 1/2011 | Sim et al. | |
| 2011/0261364 A1 | 10/2011 | Nieva et al. | |
| 2012/0121466 A1 | 5/2012 | Potyrailo et al. | |
| 2012/0208174 A1 | 8/2012 | Galush et al. | |
| 2013/0038868 A1 | 2/2013 | Schultz et al. | |
| 2013/0165329 A1 | 6/2013 | Vartak et al. | |
| 2014/0093977 A1 | 4/2014 | Raphael et al. | |
| 2014/0095100 A1 | 4/2014 | Raphael et al. | |
| 2014/0206101 A1* | 7/2014 | Liu | G01N 21/554 |
| | | | 436/501 |
| 2014/0273002 A1 | 9/2014 | Raphael et al. | |
| 2014/0327913 A1 | 11/2014 | Pacifici et al. | |
| 2015/0247846 A1 | 9/2015 | Gerion et al. | |

FOREIGN PATENT DOCUMENTS

| | | |
|---|---|---|
| CN | 1731180 A | 2/2006 |
| CN | 2758753 Y | 2/2006 |
| CN | 101617229 A | 12/2009 |
| EP | 3111214 A1 | 1/2017 |
| KR | 20160138059 A | 12/2016 |
| WO | WO-2008082713 A2 | 7/2008 |
| WO | WO-2011053894 A2 | 5/2011 |
| WO | WO-2015130980 A1 | 9/2015 |

OTHER PUBLICATIONS

Chen, et al. Ultrahigh sensitivity made simple: nanoplasmonic label-free biosensing with an extrememly low limit-of-detection for bacterial and cancer diagnostics. Nanotechnology 20 (2009) 434015 (pp. 1-9).

European Search Report dated Jun. 27, 2017 for EP Application No. 15755624.2.

Hall, et al., LSPR Biosensor Signal Enhancement Using Nanoparticle-Antibody Conjugates, J. Phys Chem C Nanomater Interfaces 2011, 115(5), pp. 1410-1414.

International search report and written opinion dated May 14, 2015 for PCT/US2015/017839.

Liu, et al., Individually color-coded plasmonic nanoparticles for RGB analysis. Chem. Commun., 2011; 47:8121-8123.

Raphael, et al. A new methodology for quantitative LSPR biosensing and imaging. Anal. Chem. 2012, 84, pp. 1367-1373.

Raphael, et al. Quantitative imaging of protein secretions from single cells in real time. Biophysical Journal, vol. 105, Aug. 2013, pp. 602-608.

Raphael, et al. Quantitative LSPR imaging for biosensing with single nanostructure resolution. Biophysical Journal, vol. 104, Jan. 2013, pp. 30-36.

Office Action dated Apr. 26, 2017 for U.S. Appl. No. 14/632,753.

U.S. Appl. No. 14/632,753 Office Action dated Dec. 19, 2017.

* cited by examiner

Surface before any reaction

Density non-detectable by spectroscopy but detectable by imaging

Density detectable by spectroscopy & imaging

|  | Index of refraction change | Predicted Peak shift [nm] | Change in Red channel value |
|---|---|---|---|
| water | 0 | 0 | 0 |
| EG 5% | 0.005 | 0.085 | 1 |
| EG 10 % | 0.01 | 0.17 | 2.5 |
| EG 20% | 0.02 | 0.34 | 5.5 |

Histogram of red pixel intensity change between images

DIGITAL LSPR FOR ENHANCED ASSAY SENSITIVITY

CROSS-REFERENCE

This application is a Continuation application of U.S. application Ser. No. 14/632,753, filed Feb. 26, 2015, which claims the benefit of U.S. Provisional Application No. 61/966,576, filed Feb. 26, 2014, and U.S. Provisional Application No. 62/108,979, filed Jan. 28, 2015, each of which is incorporated herein by reference in its entirety.

BACKGROUND OF THE INVENTION

The accuracy, sensitivity, reproducibility, and ease-of-use of instruments designed for detection and quantitation of specific molecules (e.g., analytes or markers) and/or analysis of molecular interactions are of paramount concern in a variety of fields including biomedical research, clinical diagnostics, environmental testing, and industrial process monitoring. These concerns are driven by a variety of factors including the difficulty and cost associated with producing and/or isolating molecules of interest in biomedical research, for example, or the critical impact that a diagnostic test result may have on proper diagnosis and treatment of disease in the healthcare field. Often, molecules may be present in samples of interest only at very low concentrations and may require extremely sensitive assays for detection. While a variety of assay procedures and detection techniques exist, they are often insufficient to detect analytes that are present in samples in minute quantities. Therefore, a continuing need exists to improve the sensitivity, limit of detection, quantitation, and/or time-to-result required for assay devices and instruments, and especially for those intended for use in field testing or point-of-care diagnostics testing applications. Improvements in signal amplification and/or detection techniques will play an important role in achieving these objectives.

SUMMARY OF THE INVENTION

Embodiments disclosed herein provide improved approaches for detecting and/or quantifying analytes. In many embodiments, the detection or quantitation may be accomplished with the aid of optical systems and LSPR sensors.

Thus, in one aspect, a method for detecting an analyte in a sample is provided. The method comprises: capturing a series of two or more images of a sensor surface, wherein the sensor surface is capable of sustaining a localized surface plasmon resonance; selecting one or more corresponding regions of interest in the series of two or more images; measuring a change in color within the selected regions of interest over the series of two or more images; and detecting an analyte based on the measured change in color.

In some embodiments, a limit of detection for detecting the analyte is better than 1 ng/mL. In some embodiments, a limit of detection for detecting the analyte is better than 1 pg/mL. In some embodiments, a limit of detection for detecting the analyte is better than 1 fg/mL. In some embodiments, the method further comprises determining a concentration of the analyte based on the measured change in color. In some embodiments, the change in color is a change in RGB value of pixels in the corresponding regions of interest. In some embodiments, the measured change in color is a change in color of light reflected from the sensor surface. In some embodiments, each of the selected regions of interest is an area of the sensor surface of about or less than 5 um$^2$. In some embodiments, each of the selected regions of interest is a grid of 3×3 pixels. In some embodiments, the series of two or more images are captured before and after the local analyte-induced change occurs. In some embodiments, the analyte is selected from the group consisting of a peptide, a protein, an oligonucleotide, a DNA molecule, an RNA molecule, a virus, a bacterium, a cell, a lipid molecule, a carbohydrate molecule, a small organic molecule, a drug molecule, or an ion. In some embodiments, the sensor surface is contacted with a primary binding component, the analyte, and a secondary binding component sequentially or simultaneously, wherein the secondary binding component is a sensitivity enhancing label. In some embodiments, the sensitivity enhancing label is an enzyme that catalyzes a conversion of a reactant to an insoluble product, thereby forming a precipitate on the sensor surface. In some embodiments, the sensitivity enhancing label catalyzes a reaction that results in a deposition of a polymer, a biopolymer, a chemical compound, or an enzymatic reaction product selected from a group consisting of inorganic compounds, organic compounds, chemiluminescent compounds, and fluorescent compounds. In some embodiments, the sensitivity enhancing label is a metallic nanoparticle that is capable of inducing plasmon-plasmon coupling between the metallic nanoparticle and the sensor surface. In some embodiments, the one or more corresponding regions of interest is randomly selected. In some embodiments, a plurality of corresponding regions of interest is selected. In some embodiments, the plurality of corresponding regions of interest is 10 or more corresponding regions of interest. In some embodiments, the plurality of corresponding regions of interest is 100 or more corresponding regions of interest. In some embodiments, an integration time required for capturing the series of two or more images is less than 50 ms. In some embodiments, the analyte is present in the sample in an amount of 100 ng/mL or less. In some embodiments, the analyte is present in the sample in an amount of 1 ng/mL or less. In some embodiments, the analyte is present in the sample in an amount of 1 pg/mL or less. In some embodiments, the method further comprises receiving a report comprising a result of the method and making a healthcare decision based on the reported result, wherein the sample is a patient sample.

In another aspect, a system for detecting an analyte in a sample is provided. The system comprises: a sensor surface, wherein the sensor surface is capable of sustaining a localized surface plasmon resonance; an optical imaging device, wherein the optical imaging device is capable of capturing a series of two or more images; and a processor, wherein the processor is capable of selecting one or more corresponding regions of interest in the series of two or more images, measuring a change in color within the selected regions of interest, and detecting an analyte based on the measured change in color.

In some embodiments, a limit of detection for detecting the analyte is better than 1 ng/mL. In some embodiments, a limit of detection for detecting the analyte is better than 1 pg/mL. In some embodiments, a limit of detection for detecting the analyte is better than 1 fg/mL. In some embodiments, the processor is capable of determining a concentration of the analyte based on the measured change in color. In some embodiments, the change in color is a change in RGB value of pixels in the corresponding regions of interest. In some embodiments, the sensor surface is opaque and reflects light. In some embodiments, each of the corresponding regions of interest is an area of the sensor surface of about or less than 5 um². In some embodiments, each of the corresponding regions of interest is a grid of 3×3 pixels. In some embodiments, the series of two or more images are captured before and after the change in color. In some embodiments, the analyte is selected from the group consisting of a peptide, a protein, an oligonucleotide, a DNA molecule, an RNA molecule, a virus, a bacterium, a cell, a lipid molecule, a carbohydrate molecule, a small organic molecule, a drug molecule, or an ion. In some embodiments, the system further comprises a fluidic system for delivery of a sample and assay reagents to the sensor surface, wherein the assay reagents comprise a primary binding component and a secondary binding component, and wherein the secondary binding component comprises a sensitivity enhancing label. In some embodiments, the sensitivity enhancing label is an enzyme that catalyzes a conversion of a reactant to an insoluble product, thereby forming a precipitate on the sensor surface. In some embodiments, the enzyme catalyzes a reaction that results in a deposition of a polymer, a biopolymer, a chemical compound, or an enzymatic reaction product selected from a group consisting of inorganic compounds, organic compounds, chemiluminescent compounds, and fluorescent compounds. In some embodiments, the sensitivity enhancing label is a metallic nanoparticle that is capable of inducing plasmon-plasmon coupling between the metallic nanoparticle and the sensor surface. In some embodiments, the processor is capable of randomly selecting one or more corresponding regions of interest in the series of two or more images. In some embodiments, the processor is capable of selecting a plurality of corresponding regions of interest. In some embodiments, the plurality of corresponding regions of interest is 10 or more corresponding regions of interest. In some embodiments, the plurality of corresponding regions of interest is 100 or more corresponding regions of interest. In some embodiments, an integration time of the optical imaging device is less than 50 ms. In some embodiments, the analyte is present in the sample in an amount of 100 ng/mL or less. In some embodiments, the analyte is present in the sample in an amount of 1 ng/mL or less. In some embodiments, the analyte is present in the sample in an amount of 1 pg/mL or less. In some embodiments, the sample comprises a patient sample and the detection of the analyte is used for clinical diagnostic applications.

In another aspect, a computer readable medium including code for causing a computer to execute a method is provided. The method comprises: selecting one or more corresponding regions of interest, in each of a series of two or more images of a sensor surface, wherein the sensor surface is capable of sustaining a localized surface plasmon resonance; measuring a change in color by comparing the color for corresponding regions of interest in the series of two or more images; and determining presence of an analyte based on the measured change in color.

In some embodiments, the one or more corresponding regions of interest is randomly selected. In some embodiments, a plurality of regions of interest is selected. In some embodiments, the change in color is a change in RGB value of pixels within the corresponding region of interest. In some embodiments, the change in RGB value is measured according to the formula $D=\sqrt{(\Delta R)^2+(\Delta G)^2+(\Delta B)^2}$ wherein $\Delta R$, $\Delta G$, and $\Delta B$ correspond to changes in red, green and blue pixel values in an image. In some embodiments, the method further comprises calculating a moment for the distribution of changes in RGB or greyscale values. In some embodiments, the method further comprises using pattern mining algorithms to delineate areas of the sensor surface that exhibit different responses to contact by the analyte.

In another aspect, a method for determining a concentration of an analyte in a sample is provided. The method comprises: detecting a local, analyte-induced change near a sensor surface, wherein the sensor surface is capable of sustaining a localized surface plasmon resonance; and determining a concentration of the analyte based on the local, analyte-induced change, wherein the limit of detection for the method is better than 1 fg/ml. In some embodiments, the analyte-induced change is detected with a digital imaging system.

In another aspect, a method for detection of an analyte in a sample is provided. The method comprises: capturing a series of two or more images of a sensor surface, wherein the sensor surface is capable of sustaining a localized surface plasmon resonance; and detecting a local, analyte-induced change, wherein the change is detectable in the series of two or more images.

In some embodiments, the method further comprises determining a concentration of the analyte based on the local, analyte-induced change. In some embodiments, the local, analyte-induced change is detected in a corresponding region of interest in each of the series of two or more images. In some embodiments, the region of interest is chosen randomly. In some embodiments, a plurality of regions of interest are considered. In some embodiments, a corresponding region of interest comprises one or more pixels having the same set of coordinates in each of the series of two or more images. In some embodiments, a size of the region of interest corresponds to an area of the sensor surface of about or less than 5 um². In some embodiments, a limit of detection for determining the concentration of the analyte is better than 1 fg/mL. In some embodiments, the local, analyte-induced change is a change in a dielectric constant near the sensor surface or an optical property of the sensor surface. In some embodiments, the local, analyte-induced change is a change in optical properties of light reflected from the sensor surface. In some embodiments, the change in optical property is a shift in an absorption maximum for light. In some embodiments, an absorption maximum of the sensor surface is modified by adjusting a dielectric constant of a material of which the sensor is comprised of. In some embodiments, the series of two or more images is captured using one or more components from a group comprised of light sources, lenses, mirrors, filters, beam splitters, prisms, CCD or CMOS image sensors. In some embodiments, the series of two or more images are captured before and after the local analyte-induced change. In some embodiments, a series of three or more images are captured before, during, and after the local analyte-induced change. In some embodiments, the sensor surface is contacted with a primary binding component, the analyte, and a secondary binding component simultaneously or sequentially, wherein the secondary binding component is capable of binding the analyte or an analyte-primary binding component complex, and wherein the secondary binding component comprises a sensitivity enhancing label. In some embodiments, the sensitivity enhancing label is an enzyme that catalyzes a conversion of a reactant to an insoluble product, thereby forming a precipitate on the sensor surface. In some embodiments, the sensitivity enhancing label is a metallic nanoparticle that is capable of inducing plasmon-plasmon coupling between the metallic nanoparticle and the sensor surface. In some embodiments, the sensitivity enhancing label catalyzes a reaction that results in a deposition of a polymer, a biopolymer, chemical compound, or enzymatic reaction product selected from a group comprising of inorganic compounds, organic compounds, chemiluminescent compounds, fluorescent compounds. In some embodiments, the sensitivity enhancing label are magnetic colloids, or plasmonic colloids. In some embodiments, detecting a local, analyte-induced change comprises dividing each of the series of two or more images into a plurality of regions of interests, selecting one or more regions of interests, and measuring a change in RGB and/or greyscale intensity values over the series of images within the selected regions of interests. In some embodiments, the method further comprises determining a concentration of the analyte based on the change in RGB and/or greyscale intensity values. In some embodiments, the one or more regions of interests are comprised of a grid of 3×3 pixels. In some embodiments, the one or more regions of interests are randomly selected. In some embodiments, the analyte is selected from the group consisting of a peptide, a protein, an oligonucleotide, a DNA molecule, an RNA molecule, a virus, a bacterium, a cell, a lipid molecule, a carbohydrate molecule, a small organic molecule, a drug molecule, or an ion. In some embodiments, the primary binding component is an antibody, an antibody fragment, an aptamer, a molecularly imprinted polymer, biotin, streptavidin, his-tag, chelated metal ion such as Ni-NTA, or an oligonucleotide probe. In some embodiments, the secondary binding component is an antibody, an antibody fragment, an aptamer, a molecularly imprinted polymer, biotin, streptavidin, his-tag, chelated metal ion such as Ni-NTA, or an oligonucleotide probe. In some embodiments, the sensor surface comprises adsorbed particles comprising noble metals, non-noble metals, metals, metal-oxides, metal-alloys, metal-doped semiconductors, non-metal composites, or polymers. In some embodiments, the sensor surface comprises adsorbed gold or gold-capped particles. In some embodiments, the sensor surface comprises adsorbed particles that are hollow or porous. In some embodiments, the sensor surface comprises adsorbed particles that have a core/shell structure wherein the core and shell materials are different. In some embodiments, the particles have a diameter of between about 5 nm and 2.5 um. In some embodiments, the particles are patterned or deposited by mechanical, vacuum, or chemical methods. In some embodiments, the sensor surface comprises nano or microstructures created by application of heat to metal thin films to form islands. In some embodiments, the sensor surface comprises nano or micro-structures created using lithography and etching techniques. In some embodiments, the sensor surface comprises nano or micro-structures created using nano-printing techniques. In some embodiments, the sensor surface is capable of sustaining a localized surface plasmon resonance over a portion of the sensor surface. In some embodiments, two or more samples are processed concurrently. In some embodiments, the method further comprises determining a concentration of at least a second analyte, wherein the sample comprises two or more different types of analytes.

In another aspect, an imaging system for determining concentration of an analyte in a sample is provided. The system comprises: a sensor surface, wherein the sensor surface is capable of sustaining a localized surface plasmon resonance; and a detector, wherein the detector is capable of detecting a local, analyte-induced change; and a processor, wherein the processor can determine a concentration of the analyte, wherein the limit of detection is better than 1 fg/ml.

In some embodiments, the detector comprises a digital imaging device.

In another aspect, a system for detection of an analyte in a sample is provided. The system comprises: a sensor surface, wherein the sensor surface is capable of sustaining a localized surface plasmon resonance; and an optical system, wherein the optical system is capable of capturing a series of two or more images and detecting a local, analyte-induced change in the series of two or more images.

In some embodiments, the optical system comprises a processor for processing the series of two or more images and determining a concentration of the analyte based on the local-analyte induced change. In some embodiments, the local, analyte-induced change is detected in a corresponding region of interest in each of the series of two or more images. In some embodiments, the region of interest is chosen randomly. In some embodiments, a plurality of regions of interest are considered. In some embodiments, a corresponding region of interest comprises one or more pixels having the same set of coordinates in each of the series of two or more images. In some embodiments, a size of the region of interest corresponds to an area of the sensor surface of about or less than 5 $um^2$. In some embodiments, a limit of detection for determining the concentration of the analyte is better than 1 fg/mL. In some embodiments, the local, analyte-induced change is a change in a dielectric constant near the sensor surface or optical property of the sensor surface. In some embodiments, the local, analyte-induced change is a change in optical properties of light reflected from the sensor surface. In some embodiments, the change in optical property is a shift in an absorption maximum for light. In some embodiments, an absorption maximum of the sensor surface is modified by adjusting a dielectric constant of a material of which a sensor is comprised of. In some embodiments, the optical system comprises light sources, lenses, mirrors, filters, beam splitters, prisms, CCD and/or CMOS image sensors. In some embodiments, the series of two or more images are captured before and after the local analyte-induced change. In some embodiments, a series of three or more images are captured before, during, and after the local analyte-induced change. In some embodiments, the system further comprises a fluidic system for delivery of a sample and assay reagents to the sensor surface. In some embodiments, the assay reagents comprise a primary binding component and a secondary binding component, and wherein the secondary binding component comprises a sensitivity enhancing label. In some embodiments, the sensor surface is contacted with the primary binding component, the analyte, and the secondary binding component simultaneously or sequentially. In some embodiments, the sensitivity enhancing label is an enzyme that catalyzes a conversion of a reactant to an insoluble product, thereby forming a precipitate on the sensor surface. In some embodiments, the sensitivity enhancing label is a metallic nanoparticle that is capable of inducing plasmon-plasmon coupling between the metallic nanoparticle and the sensor surface. In some embodiments, the sensitivity enhancing label catalyzes a reaction that results in deposition of a polymer, a biopolymer, chemical compound, or enzymatic reaction product selected from a group comprising of inorganic compounds, organic compounds, chemiluminescent compounds, fluorescent compounds. In some embodiments, the sensitivity enhancing labels are magnetic colloids, or plasmonic colloids. In some embodiments, the optical system comprises a processor capable of dividing each of the series of two or more images into a plurality of regions of interests, selecting one or more regions of interests, and measuring a change in RGB and/or greyscale intensity values over the series of images within the selected regions of interest. In some embodiments, the processor is further capable of determining a concentration of the analyte based on the measured change in RGB and/or greyscale intensity values. In some embodiments, the one or more regions of interest are comprised of a grid of 3×3 pixels. In some embodiments, the one or more regions of interest are randomly selected. In some embodiments, the magnitude of the change in RGB and/or greyscale intensity values are correlated with a concentration of the analyte in the sample. In some embodiments, the analyte is selected from the group consisting of a peptide, a protein, an oligonucleotide, a DNA molecule, an RNA molecule, a virus, a bacterium, a cell, a lipid molecule, a carbohydrate molecule, a small organic molecule, a drug molecule, or an ion. In some embodiments, the primary binding component is an antibody, an antibody fragment, an aptamer, a molecularly imprinted polymer, biotin, streptavidin, his-tag, chelated metal ion such as Ni-NTA, or an oligonucleotide probe. In some embodiments, the secondary binding component is an antibody, an antibody fragment, an aptamer, a molecularly imprinted polymer, biotin, streptavidin, his-tag, chelated metal ion such as Ni-NTA, or an oligonucleotide probe. In some embodiments, the sensor surface comprises adsorbed particles comprising noble metals, metals, metal-oxides, metal-alloys, metal-doped semiconductors, non-metal composites, or polymers. In some embodiments, the sensor surface comprises adsorbed gold or gold-capped particles. In some embodiments, the sensor surface comprises adsorbed particles that are hollow or porous. In some embodiments, the sensor surface comprises adsorbed particles that have a core/shell structure wherein the core and shell materials are different. In some embodiments, the particles have a diameter of between about of 5 nm and 2.5 um. In some embodiments, the particles are patterned by mechanical, vacuum, or chemical methods. In some embodiments, the sensor surface comprises nano or micro-structures created by application of heat to metal thin films to form islands. In some embodiments, the sensor surface comprises nano or micro-structures created using lithography and etching techniques. In some embodiments, the sensor surface comprises nano or micro-structures created using nano-printing techniques. In some embodiments, the sensor surface is capable of sustaining a localized surface plasmon resonance over a portion of the sensor surface. In some embodiments, two or more samples are processed concurrently. In some embodiments, the system is further configured to determine a concentration of at least a second analyte, wherein the sample comprises two or more different types of analytes.

In another aspect, a computer readable medium including code for causing a computer to execute a method is provided. In some embodiments, the method comprises: selecting a region of interest comprising one or more image pixels in each of a series of two or more images of a sensor surface, wherein the sensor surface is capable of sustaining a localized surface plasmon resonance; and measuring a change in RGB or greyscale values by comparing the RGB or greyscale values for corresponding regions of interest in the series of two or more images.

In some embodiments, the method further comprises generating a histogram of the number of analysis regions in a complete image of the sensor surface for which a specified change in RGB or greyscale value is measured. In some embodiments, the method further comprises determining an analyte concentration. In some embodiments, the change in RGB value is calculated according to the formula $D=\sqrt{(\Delta R)^2+(\Delta G)^2+(\Delta B)^2}$ wherein $\Delta R$, $\Delta G$, and $\Delta B$ correspond to changes in red, green and blue components in an image. In some embodiments, the method further comprises calculating a moment for the distribution of changes in RGB or greyscale values. In some embodiments, the method further comprises using pattern mining algorithms to delineate areas of the sensor surface that exhibit different responses to contact by an analyte.

In another aspect, a method for determining concentration of an analyte in a sample is provided. The method comprises: detecting an analyte-induced change near a sensor surface, wherein the analyte-induced change is an RGB color change detected with an imaging system; and determining a concentration of the analyte based on changes detected in step (a), wherein the limit of detection for the method is less than 1 fg/ml.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
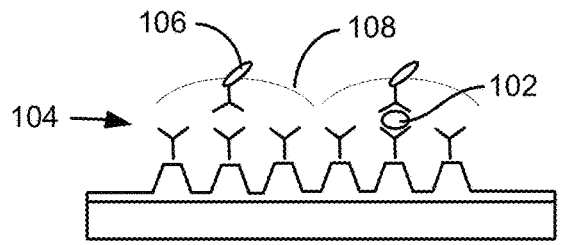
FIG. 1 illustrates an ELISA assay format used in conjunction with LSPR sensors, in accordance with embodiments.

The methods, devices, and systems of the present disclosure provide detection and quantitation of analytes present in small quantities in a sample. While the present disclosure may refer to detection and quantitation of analytes present in small quantities in a sample, it is to be understood that this refers to the capabilities of the methods, devices, and systems mentioned herein and is understood not to be a limitation. Therefore, the methods, devices, and systems of the present disclosure may be used for detection and/or quantitation of analytes present in small, moderate, or large quantities in a sample. The analyte may be any molecule of interest. The analyte may be a peptide, a protein, an oligonucleotide, a DNA molecule, an RNA molecule, a virus, a bacterium, a cell, a lipid molecule, a carbohydrate molecule, a small organic molecule, a drug molecule, or an ion. An analyte presence may be detected using various sensors. Previously, sensors exploiting the phenomenon of localized surface plasmon resonance (LSPR) to optically detect binding of analyte molecules to a sensor surface have been studied.

Surface plasmons are coherent, delocalized electron oscillations that exist at the interface between a negative and positive permittivity material. For example, surface plasmons may exist at a metal-dielectric interface such as a thin metal film exposed to an aqueous solution. Surface plasmon resonance may occur when the electron oscillations are induced by incident light, where the frequency of the incident photons matches the natural frequency of surface electrons oscillating against the restoring force exerted by positively charged nuclei distributed within the metal. Localized surface plasmon resonance may occur at the surface of small metallic nanoparticles or nanostructured surfaces upon excitation by light of the appropriate frequency.

LSPR sensors rely on the extreme sensitivity of the position of the surface plasmon absorption maximum to the local environment in the immediate vicinity of the interface. In particular, the signal transduction mechanism in LSPR sensors may often associated with a change in the index of refraction (or dielectric constant) near an LSPR-active surface. The signal transduction mechanism in LSPR sensors may be associated with a change in an optical property of the sensor surface (e.g., shift in an absorption maximum for light) or a change in optical properties of light reflected from the LSPR-active surface. An LSPR-active surface may refer to an LSPR sensor surface. If an LSPR sensor surface is placed in contact with a film or solution of index of refraction $n_1$, followed by deposition on the surface of a material having an index of refraction $n_2$, the wavelength of the plasmon absorption maximum shifts by a value $\Delta\lambda$. It is possible to link the plasmon shift to the change in index of refraction $\Delta n = n_2 - n_1$ through the following relation:

$$\Delta\lambda = m * \Delta n [1 - e^{(-2L/\delta)}] \quad (1)$$

where m is a constant representing the sensitivity of the sensor, L is the thickness of the deposited material with index of refraction $n_2$, and $\delta$ is the decay length of the evanescent plasmon field. In addition to monitoring the shift in absorption maximum, in some cases, the change in index of refraction (or dielectric constant) near the sensor surface may be detected by monitoring other optical properties, for example, changes in reflection angle of the incident light, changes in the intensity of transmitted or reflected light, changes in the polarization of light reflected from the surface, etc. The optical properties of the surface, or of light transmitted or reflected by the surface, may then be monitored using any of a variety of light sources and detectors as described further blow.

LSPR sensors may be used in conjunction with various signal amplification techniques (e.g., ELISA assays). FIG. 1 illustrates an ELISA assay format used in conjunction with LSPR sensors, in accordance with embodiments. The ELISA assay format is a popular assay technique for the detection of analytes that relies on signal amplification to increase assay sensitivity. In some embodiments of the methods and systems disclosed herein, nanostructured LSPR sensor surfaces are combined with the immuno-precipitation ELISA assay format and a digital detection scheme to achieve very low detection limits (e.g. in the fg/ml range). In an ELISA assay, a primary antibody directed towards the analyte of interest 102 may be used to capture the analyte on the sensor surface 104, and a secondary antibody that is conjugated to a sensitivity enhancing label 106 may bind to the immobilized analyte. The sensitivity enhancing label may be, for example, an enzyme that catalyzes the conversion of a soluble reactant to an insoluble product that forms deposits on the sensor surface near the location of the immobilized enzyme. The LSPR sensor may be utilized in detecting a change (e.g., index of refraction, dielectric constant, etc) at the sensor surface which results from formation of the deposits 108. In some embodiments of the disclosed methods and devices, the enzyme used as a sensitivity enhancing label is alkaline phosphatase, which catalyzes the conversion of a mixture of 5-bromo-4-chloro-3'-indolyphosphate (BCIP) and nitro-blue tetrazolium (NBT) into a mixture of insoluble products.

It may be instructive to estimate numerical values for the expected peak wavelength shift when a thin immuno-precipitate forms at the LSPR surface. For small deposits, equation (1) can be linearized and reduces to $$\Delta\lambda = m * \Delta n \frac{2L}{\delta} \quad (2)$$

Using m/$\Delta$n=200, $\Delta$n=0.15 for deposition of BCIP/NBT with $n_2$~1.48 and $n_1$=1.33, $\delta$~30 nm and L=5 nm, $\Delta\lambda$~10 nm is obtained. Thus, a 5 nm deposit may be predicted to generate a plasmon wavelength shift of ~10 nm. In practice, wavelength shifts of up to 50-80 nm may be observed. The implementation of immuno-precipitation ELISA assay formats on LSPR sensor surfaces has been found to improve the limit of detection for several assays by about 1 order of magnitude over that achieved using a conventional ELISA.

Figure 2:
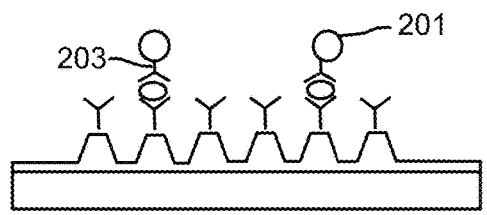
FIG. 2 illustrates plasmon-plasmon coupling sandwich assay used in conjunction with LSPR sensors, in accordance with embodiments.

In addition to being sensitive to local refractive index changes as discussed above, there may be other transduction mechanisms that are able to generate large localized surface plasmon resonance shifts. For example, plasmon-plasmon coupling may also generate large localized plasmon resonance shifts. FIG. 2 illustrates plasmon-plasmon coupling sandwich used in conjunction with LSPR sensors, in accordance with embodiments. In this implementation, a plasmonic moiety 201, e.g. a particle capable of sustaining surface plasmons such as a colloidal gold or silver particle, is conjugated to the secondary antibody 203 as a sensitivity enhancing label. Strong coupling between the particle plasmons and sensor surface plasmons occurs when the secondary antibody is immobilized on the surface, and results in the measurements of large plasmon shifts.

As an illustrative example, consider a plasmonic particle such as a 40 nm gold colloid. When streptavidin binds to the surface of the 40 nm gold colloid, it produces approximately a 2 nm shift in the plasmon position of the gold colloid. In contrast, if streptavidin is attached to a 40 nm gold colloid and this biomolecule-gold colloid conjugate is brought into contact with a second plasmonic particle, the plasmon-plasmon coupling between colloidal particles produces an exceedingly large plasmon shift, potentially in excess of 70 nm. This phenomenon has been reported in the technical literature using pairs of colloidal particles in solution, and for other configurations with one colloidal particle in solution and a plasmonic partner on a surface.

Both signal amplification mechanisms described above (i.e. the use of conjugated enzymes as sensitivity enhancement labels to catalyse reactions leading to local refractive index changes, and the use of conjugated metal nanoparticles to produce plasmon-plasmon coupling) result in plasmon shifts that can reach tens of nanometers in magnitude. The enhanced localized surface plasmon resonance shifts are associated with an enhanced limit of detection (LOD) in bioassays. In general, the LOD for ELISA assays performed on nanostructured LSPR surfaces are in the (sub-)pg/mL analyte range. For an average analyte of ~60 kDa, these LOD correspond to approximately $10^{10}$ analyte molecules per milliliter of solution.

Most LSPR instruments utilized as sensors may measure an analogue signal. The analogue signal may signify that the recorded signal is an average signal resulting from the binding of multiple analyte molecules on the surface. Individual binding events occur as random processes in time and space, and may not themselves be directly detectable by known detection schemes. Over time, the randomness may give rise to a well-defined average number of immobilized molecules on the surface. When the average number of immobilized molecules passes above the limit of detection, the instruments may yield a positive reading. Conversely, when the average number of immobilized molecules does not pass above the limit of detection (e.g., due to low concentration of analytes), the instruments may yield negative readings despite the presence of analytes.

Figure 3:
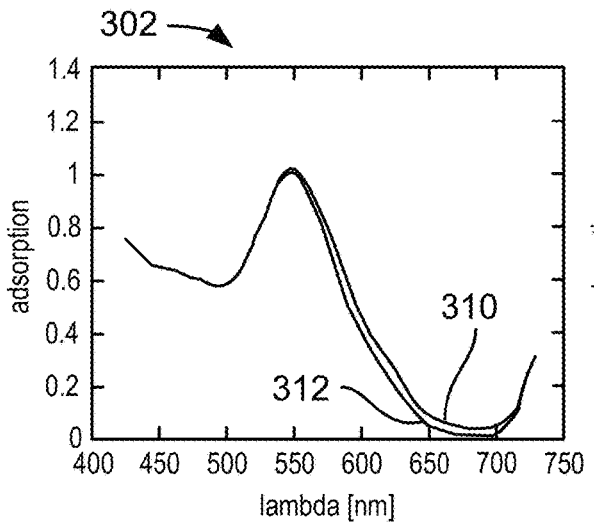
FIG. 3 shows extinction of white light reflected from an assay surface resulting from immobilization of an antigen at two different concentrations, in accordance with embodiments.
Figure 3:
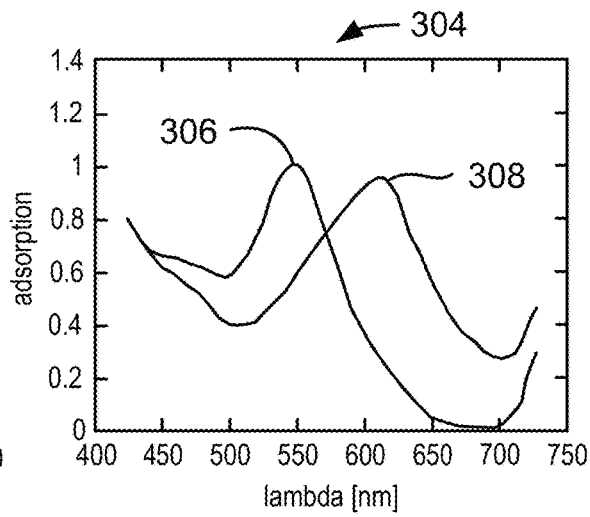

FIG. 3 shows extinction of white light reflected from an assay surface resulting from immobilization of an antigen at two different concentrations, in accordance with embodiments. An analogue signal is measured (e.g., via spectroscopic detection) for antigen concentrations that are low 302 and high 304. For each antigen concentration, the extinction of white light from the assay surface is measured before and after the amplification. At high antigen concentrations, the extinction of white light from the assay surface measured before amplification 306 is clearly different from the extinction of white light from the assay surface that is measured after amplification 308. However, for the low antigen concentration 108, the extinction of white light from the assay surface measured before amplification 310 is indistinguishable from that measured after amplification 312.

Plasmon shifts resulting from a change in refractive index or of from plasmon-plasmon coupling may not depend on the size of the LSPR sensing area (e.g., as shown by equation (1)). LSPR sensing areas as small as 20 nm have been successfully demonstrated. A difficulty with using such small sensing areas may be that the number of photons collected is small. Therefore, analogue spectral analysis to measure peak shifts may require long integration times of much greater than 1 min. For precision measurements required in a quantitative assay, the number of signal measurements required to reduce the intrinsic noise in the optical detection through signal averaging may bring the total signal collection time to greater than 10-100 minutes, since the signal to noise ratio scales as the number of signal sampling repeats (e.g., $S/N \sim \sqrt{repeats}$).

When a limited number of photons are reflected from a sensor surface (e.g., due to low concentration of analytes or small sensor surface), a digital detection scheme (e.g., digital LSPR) may be utilized. The digital detection scheme may enable the detection of individual binding events, and/or the detection of binding events in a local area (small sensing area). The binding of a single molecule to its ligand is a binary or digital process (e.g., it either binds or not). The ability to detect individual binding events therefore, may enable achievement of the assay sensitivity previously unattained.

Figure 4:
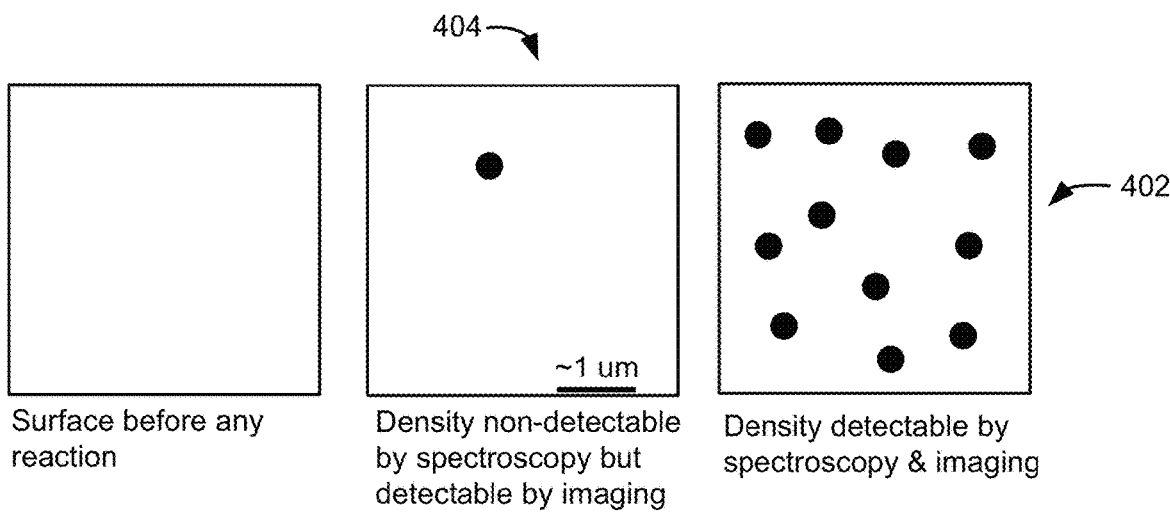
FIG. 4 illustrates the principle of digital LSPR, in accordance with embodiments

FIG. 4 illustrates the principle of digital LSPR, in accordance with embodiments. In some embodiments, detection of analyte-induced optical properties (e.g. shifts in the plasmon resonance peak wavelength) may utilize white light illumination, an optical system capable of forming a magnified image of the LSPR sensor surface, a color or grey scale CCD or CMOS camera to capture images, and an algorithm that measures the change in RGB or grey scale values for each pixel of the image. In digital LSPR, an insoluble product or a strong plasmon-plasmon coupling may create or induce a local change in index of refraction of the LSPR-active surface that manifests itself as a local area with a distinct color shift (e.g., the black spots in FIG. 4) that is detectable under magnification. If the concentration of an analyte is high (e.g., in the pg/ml range), the surface density of immobilized analyte molecules may be such that the entire sensor surface 402 is covered with black spots, and analytes may be detectable with traditional spectroscopic means as well as with digital detection schemes. If however, the number of antigen captured by the surface is small (e.g. at analyte concentrations of a few fg/ml or lower), localized color shifts may not be resolved with spectroscopic means but may be detected digitally as shown in 404.

For a digital detection scheme mentioned herein, local spectrometric shifts of 1-5 nm may be equivalent to local color changes that can be captured in a color image and quantified through a change in RGB or greyscale values for pixels. For example, local spectrometric shifts of about 5 nm may correlate to a change in RGB value of about 1 to 3 (out of 255) for one or more pixels corresponding to the location of the immobilized analyte molecule in a magnified image of the sensor surface. Measuring the color or intensity for an individual image sensor pixel may require fewer photons than measuring the full spectrum of the light impinging on it. Hence, digital color and/or intensity detection may provide an advantage of a fast sampling rate compared to traditional spectral detection. However, both digital and spectral detection methods contain similar information (e.g., spectrometric shifts). Therefore, digital detection may offer a superior method for detecting resonance peak shifts of greater than 5 nm for sensing areas in the um$^2$ range and below, where the photon count is limited.

Digital detection schemes may use LSPR sensors. The LSPR sensors may comprise LSPR active surfaces. An LSPR active surface may be any surface that is capable of sustaining a localized surface plasmon resonance. The localization of surface plasmons in LSPR sensors derives from the use of metallic nanoparticles or nanostructured metallic surfaces. As will be described more fully below, there exists a variety of approaches known to those of skill in the art for fabricating suitable sensor surfaces that are capable of sustaining a localized surface plasmon resonance, see for example, Takei, et al., U.S. Pat. No. 6,331,276, which is incorporated by reference in its entirety herein. The components required to fabricate a nanostructured LSPR sensor may include substrates, metal layers or films, nanoparticles or nanostructures, and/or other dielectric or insulating materials.

The LSPR active surface may comprise a sensor substrate. Nanostructured LSPR sensor substrates may be fabricated using a variety of materials, including, but not limited to, glass, fused-silica, silicon, ceramic, metal, or a polymer material. In some embodiments, it is desirable for the substrate material to be optically transparent so that the sensor surface may be illuminated from the back side. In other embodiments, the sensor surface is illuminated from the front side, and the transparency or opacity of the substrate material is not important. In some embodiments, it may be desirable to measure properties of light that is transmitted through the sensor surface. In some embodiments, it may be desirable to measure properties of light that is reflected from the sensor surface. For example, measuring properties of light reflected from the sensor surface may be superior than measuring light transmitted through the sensor surface in terms of plasmonic response to an analyte. In general, the substrates used for fabricating nanostructured LSPR sensors will have at least one flat surface. However, in some embodiments, the substrate may have a curved surface (e.g., a convex surface or a concave surface, or a surface of some other geometry).

Nanostructured LSPR sensors may comprise one or more metal layers or metallic thin films. In some embodiment, there may be about 1, 2, 5, 10, 15, 20, or more metal layers. In some embodiments, the preferred metal for use in layers or films will be noble metals such as gold, silver, platinum, palladium, and the like. In some embodiments, non-noble metals, e.g. copper, may be used. One advantage of using a noble metal may be their ability to support surface plasmon activity due to the high mobility of conductance band electrons. For some noble metals, an additional advantage is their ability to resist chemical corrosion or oxidation. The metal layers or metallic thin films may comprise any mixture and/or any combination of the preferred metals mentioned herein. For example, the metal layer may comprise of one layer of gold, one layer of copper, and one layer of a mixture of silver and platinum. Metal layers or films may be fabricated by any of the techniques known to those of skill in the art, including, but not limited to, thermal, electroplating, sputter coating, chemical vapor deposition, vacuum deposition, and the like. The thin film may be of thickness between 5 and 500 nm.

In some embodiments, nanostructured LSPR sensors will include one or more layers of a dielectric (insulating) material. Any wide variety of materials may be used to create a dielectric material, including, but not limited to, glass, ceramic, silicon, or polymer materials such as polyimides, heteroaromatic polymers, poly(aryl ether)s, fluoropolymers, or hydrocarbon polymers lacking polar groups. Polymer layers or thin films may be fabricated by a variety of techniques known to those of skill in the art, including, but not limited to, solution casting and spin coating, chemical vapor deposition, plasma enhanced chemical vapor deposition, and the like. In some embodiments, the surface plasmon resonance properties of a nanostructured LSPR sensor (e.g., resonance wavelength, absorption maximum, etc) may be tuned by adjusting the thickness or dielectric constant of the material used to form an insulating layer between two metallic layers.

In some embodiments, nanostructured or microstructured surfaces may be prepared by adsorbing or attaching particles (e.g., nanoparticles or fine particles) to substrate surface. The particles may be of any variety and of any shape including, but not limited to, spherical, non-spherical, cubic, cuboid, pyramidal, cylindrical, conical, oblong, star-shaped, in the form of short nanowires, hollow, porous, and the like. Nanoparticles may be particles of diameter ranging from 5 to 500 nanometers. Fine particles may be particles of diameter ranging from 500 to 2,500 nanometers. Any of a number of different particle types may be used, including, but not limited to, metals, noble metals, metal-oxides, metal-alloys, metal-doped semiconductors, non-metal composites, polymers, gold or silver colloids, dielectric nanoparticles and microparticles, semiconductor nanoparticles, and hybrid structures such as core-shell nanoparticles, many of which are available commercially or can be prepared by any of a variety of methods known to those of skill in the art. Hybrid structures may be composed of different material. For example, a core-shell nanoparticle may be comprised of a solid outer shell and a liquid inner core.

In some embodiments, nanostructured LSPR surfaces are prepared by adsorbing or attaching nanoparticles (e.g., non-metallic nanoparticles) to a substrate surface and coating or partially-coating the attached particles with a thin metallic film to create a capped-particle surface, e.g. a gold-capped particle surface. The nanoparticles may be coated with one or more layers of the thin metallic film. For example, the nanoparticles may be coated with about 1, 2, 5, 10, 20 or more layers of the thin metallic film. In some embodiments, the preferred metal for use in the thin metallic film will be noble metals such as gold, silver, platinum, palladium, copper, and the like. The thin metallic film may comprise any mixture and/or any combination of the preferred metals mentioned herein. For example, the thin metallic film may comprise of one layer of gold, one layer of copper, and one layer of a mixture of silver and platinum. The coating may be of thickness between 5 nm and 200 nm. In some embodiments, the nanostructured surface may cover the entire substrate surface. In other embodiments, the nanostructured surface may cover only a portion of the substrate surface, and may be distributed across the substrate surface in a predefined pattern.

In some embodiments, rather than utilizing nanoparticle adsorbed or attached to a surface to create nanostructured LSPR surfaces, the nanostructured surface may be fabricated using any of a variety of techniques known to those of skill in the art (e.g., patterned by mechanical, vacuum, or chemical methods). Nanostructures such as cylindrical columns or pillars, rectangular columns or pillars, cylindrical or rectangular nanowells, and the like may be fabricated in a variety of substrate materials using techniques such as lithography, etching, and/or printing. For example, nanostructures may be fabricated using photolithography and wet chemical etching, reactive ion etching, or deep reactive ion etching, focused ion beam milling, application of heat to metal thin films to form islands, dip-pen nanolithography, nano-printing, and the like.

The dimensions of the aforementioned nanostructures may range from a few nanometers to hundreds of nanometers. In some embodiments, the nanostructured surface may cover the entire substrate surface. In other embodiments, the nanostructured surface may cover only a portion of the substrate surface, and may be distributed across the substrate surface in a predefined pattern. The sensor surface may be capable of sustaining a localized surface plasmon resonance over all or portion of the sensor surface. The nanostructured surface may be of high or low density. To measure properties of light transmitted through a sensor surface, having a nanostructured surface of low density may be desired. To measure properties of light reflected from a sensor surface, having a nanostructured surface of high density may be desired. A surface having a high density of nanostructures may absorb and scatter light efficiently. In some embodiments, it may be desirable to measure properties of light that is transmitted through the sensor surface. In some embodiments, it may be desirable to measure properties of light that is reflected from the sensor surface. For example, measuring properties of light reflected from the sensor surface may be superior than measuring light transmitted through the sensor surface in terms of plasmonic response to an analyte.

The LSPR active surface may be created in a variety of ways and/or steps. As an illustrative example, a method of creating one type of LSPR active surface mentioned herein may comprise 1) the deposition of a thin film of AU in the range of 5-500 nm thick, 2) chemistry deposition of nanometer size silica or polymer particles (~10 to 2500 nm in size) in a random, close-packed configuration, and 3) capping of the silica or polymer particles with one or more layers of Au (~5 to 200 nm thick).

As described above, a variety of assay formats may be implemented using nanostructured LSPR sensors as a detector, including, but not limited to, sandwich immunoassays, enzyme-linked immunosorbent (ELISA) assays, electrochemical assays, and the like. Many of these assay formats require the use of affinity reagents (or binding components), e.g. antibodies, to confer binding specificity for the analyte of interest to the sensor surface.

Assays for the detection and quantitation of analytes in a variety of samples may be implemented using nanostructured LSPR sensors or devices that incorporate nanostructured LSPR sensors. Examples of samples include air, gas, water, soil, or industrial process stream samples, as well as biological samples such as tissue, cells, or any bodily fluid, such as blood, sweat, tears, urine, or saliva.

Assays for the detection and quantitation of a variety of analytes (markers, biomarkers) may be implemented using nanostructured LSPR sensors, including, but not limited to, a peptide, a protein, an oligonucleotide, a DNA molecule, an RNA molecule, a virus, a bacterium, a cell, a lipid molecule, a carbohydrate molecule, a small organic molecule, a drug molecule, or an ion.

Any of a variety of affinity reagents, affinity tags, or primary binding components may be used for recognition and binding of the target analyte with high specificity and high affinity, including, but not limited to antibodies, antibody fragments, aptamers, molecularly imprinted polymers, biotin, streptavidin, his-tags, chelated metal ions such as Ni-NTA, or oligonucleotide probes. In some embodiments, one or more primary binding components may be pre-immobilized on the sensor surface prior to performing an assay. In some embodiments, one or more primary binding components may be mixed with the sample prior to contacting the sensor surface with the sample (e.g., as part of the assay procedure).

In some embodiments, a variety of affinity reagents, affinity tags, or secondary binding components may also be used to confer high specificity and enhanced sensitivity to the performance of the nanostructured LSPR sensor. In some embodiments, the secondary binding component may be conjugated to a sensitivity enhancing label to yet further increase the sensitivity of the assay. Examples of suitable secondary binding components for use in the methods and devices disclosed herein include, but are not limited to, antibodies, antibody fragments, aptamers, molecularly imprinted polymer beads, biotin, streptavidin, his-tags, chelated metal ions such as Ni-NTA, oligonucleotide probes. Examples of sensitivity enhancing labels include (i) enzymes which catalyze the conversion of a non-detectable reactant to a detectable reaction product, e.g. an insoluble precipitate that forms deposit on the nanostructured LSPR sensor surface, and (ii) metallic nanoparticles or microparticles which are capable of inducing plasmon-plasmon coupling with the sensor surface. The sensitivity enhancing labels may catalyze reactions that result in a deposition of a polymer, biopolymer, chemical compound, or enzymatic reaction products selected from a group including, but not limited to inorganic compounds, organic compounds, chemiluminescent compounds, fluorescent compounds, magnetic colloids, and plasmonic colloids. Examples of enzymes that may be suitable for use as sensitivity enhancing labels include, but are not limited to, alkaline phosphatase and horse radish peroxidase. Examples of reactants that may be suitable for enzymatic conversion to an insoluble precipitate that may form deposits on the sensor surface include, but are not limited to, 5-bromo-4-chloro-3'-indolyphosphate (BCIP) and nitro-blue tetrazolium (NBT), or mixtures thereof, which are converted to an insoluble precipitate by alkaline phosphatase.

Figure 5:
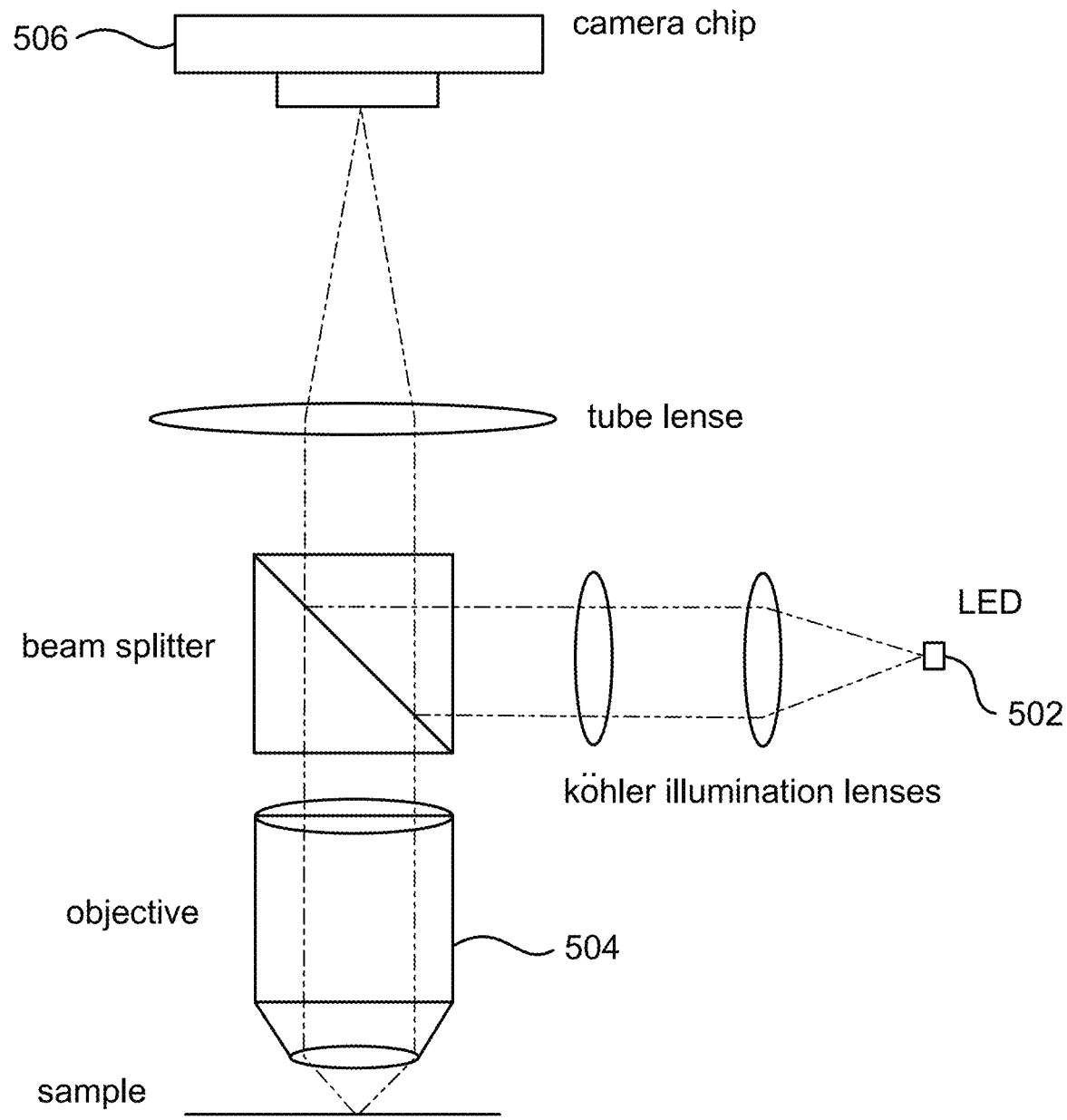
FIG. 5 shows an optical system, in accordance with embodiments.
Figure 6:
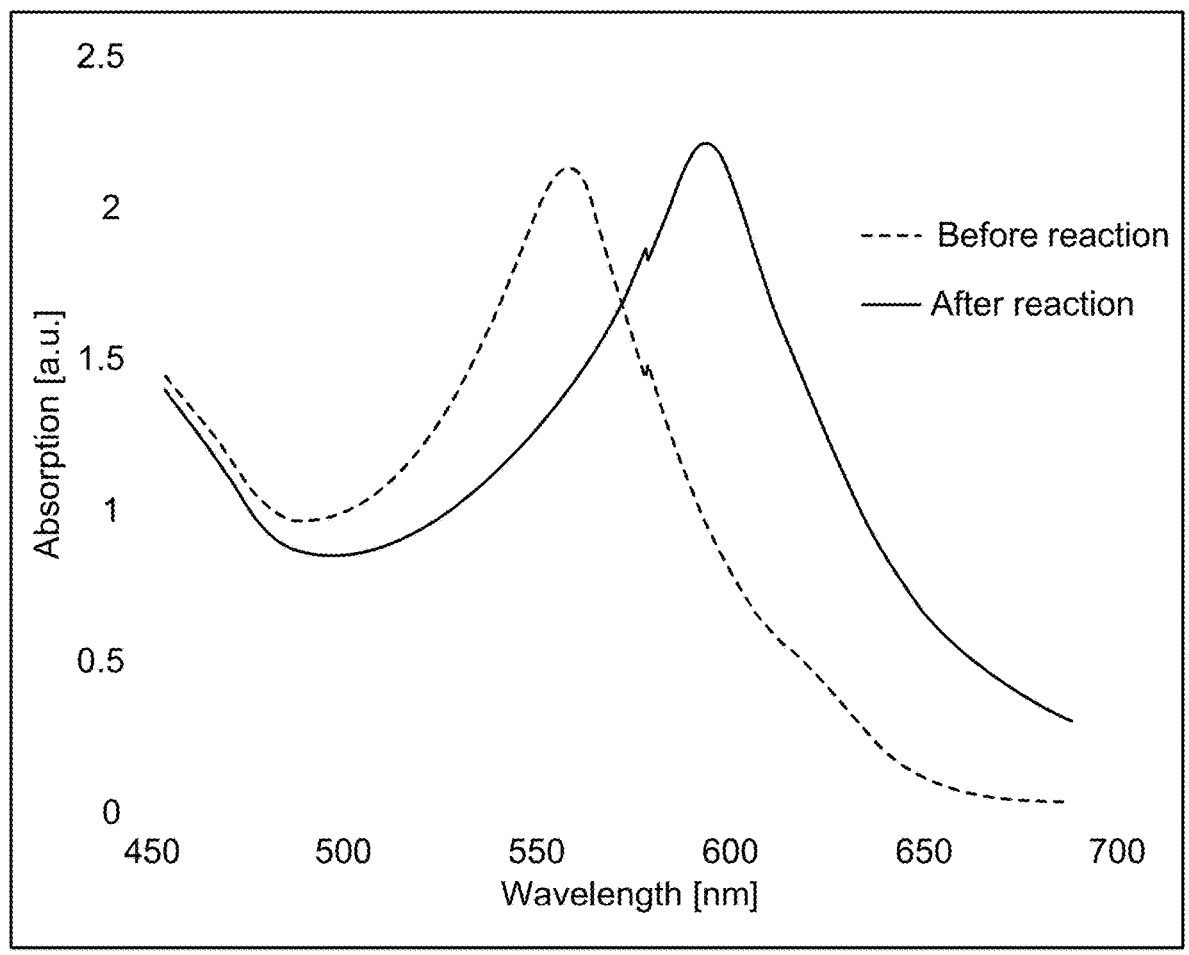
FIG. 6 shows the absorption of light directed at the sensor surface before a reaction (e.g., ELISA reaction) that is different from absorption of light directed at the sensor surface after a reaction, in accordance with embodiments.

The methods and systems described herein may make use of LSPR capable surfaces coupled with optical systems. Optical systems may refer to a digital imaging system. FIG. 5 shows an optical system, in accordance with embodiments. An optical system may comprise a light source 502, an objective lens 504, mirrors, filters, beam splitters, prisms, detectors (e.g., CCD, CMOS sensors) 506, and/or stages that may be scanned or maintained fixed with respect to a detector. The light source may be an LED, laser, halogen source, or other light sources. The light source may direct light at the sensor surface before and after an amplification of signal takes place (e.g. plasmon-plasmon coupling or ELISA reaction). The light source may direct light from the substrate side or from the sensor surface side. FIG. 6 shows the absorption of light directed at the sensor surface before a reaction 601 (e.g., ELISA reaction) that is different from absorption of light directed at the sensor surface after a reaction 603, in accordance with embodiments. Due to deposition of precipitation on the LSPR active surface, the absorption peak is shifted up from around 550 nm before the reaction, to around 600 nm after the reaction.

The light source may be placed such that light is generally incident on the LSPR surface at 90 degrees. Similarly, a detector may be placed such that it detects light that is reflected from the surface at 90 degrees. The light source may be placed such that light is generally incident on the LSPR surface at an oblique angle. The light may be configured to be narrow and collimated. Similarly, the detector may be placed such that it detects the reflected light form the surface at an oblique angle. The light source may be directed through an optical channel or an optical fiber. The optical channel or optical fiber may then be positioned so that light exits the optical channel or optical fiber and is incident on the LSPR surface at the desired angle.

A detector may detect a shift in the optical absorption peak before and after the plasmon-plasmon coupling or the ELISA reaction. The detector may detect any optical property of light, such as absorption peak, angle of reflected light, and polarization properties of light. The detector may comprise an image sensor. An image sensor may be a CCD sensor, CMOS sensor, or NMOS sensor. The image sensor may capture a series of images of the sensor surface. The series of images may be greyscale images. The series of images may be RGB images. The series of images may comprise image frames that correspond to images captured before, during, and after an assay is completed with the analyte. The series of images described herein may be of sufficient detail such that a change due to an analyte can be detected over the series of time lapse images. The series of images may comprise about or more than 1000 images, 500 images, 400 images, 300 images, 200 images, 100 images, 50 images, 10 images, 5 images, 4 images, 3 images, or 2 images. The image sensor may capture the series of image frames at a predefined capture rate. The inverse of the capture rate may be 1 millisecond per frame, 2 milliseconds per frame, 5 milliseconds per frame, 10 milliseconds per frame, 20 milliseconds per frame, or 50 milliseconds per frame. Image sensors may vary in terms of pixel size and pixel count. The image resolution may depend on the pixel size and pixel count. Image sensors may have a pixel count of about or more than 0.5 mega pixels, 1 mega pixels, 4 mega pixels, 10 mega pixels, 20 mega pixels, 50 mega pixels, 80 mega pixels, 100 mega pixels, 200 mega pixels, 500 mega pixels, or 1000 mega pixels. The pixel size corresponding to the image sensor may be about or less than 5 microns, 3.5 microns, 2 microns, 1 micron, 0.5 microns, or 0.1 micron.

The objective lens may provide a magnification of the sensor surface. The objective lens may have long working distance (e.g., 2-5 mm) to zoom in on a sensor surface. The long working distance may provide enough clearance to accommodate sample-handling (e.g., with fluidics). The objective lens may be optimized for near-field imaging. The magnification may provide magnification that is about or more than 5×, 10×, 20×, 50×, 100×, or 200× of the sensor surface. The magnification of the objective enables each pixel of the image frame to correspond to a surface area that is much smaller than the pixel size. For examples, an image sensor with a pixel size of 5 microns capturing an image under a 10× objective will produce an image with a pixel that corresponds to a sensor surface of 0.25 um$^2$. This magnification may enable local areas on the LSPR surface corresponding to enzyme activity or plasmon-plasmon coupling to be clearly distinguishable and counted.

The series of images acquired by the optical system may be analyzed using an algorithm. The algorithm may be stored in a computer readable medium. The computer readable medium may be any medium capable of storing data in a format that may be read or processed by a device (e.g., compact disc, floppy disk, usb flash drive, hard disk drive, etc). The algorithms mentioned herein may comprise pattern mining algorithms that delineate areas of the sensor surface that exhibit response to contact by an analyte. The pattern mining algorithms may manipulate changes in RGB or greyscale values to determine specific patterns on an image (e.g., determining areas of an LSPR sensor surface for which image pixels have undergone a change in red pixel value within a certain defined range).

Figure 7:
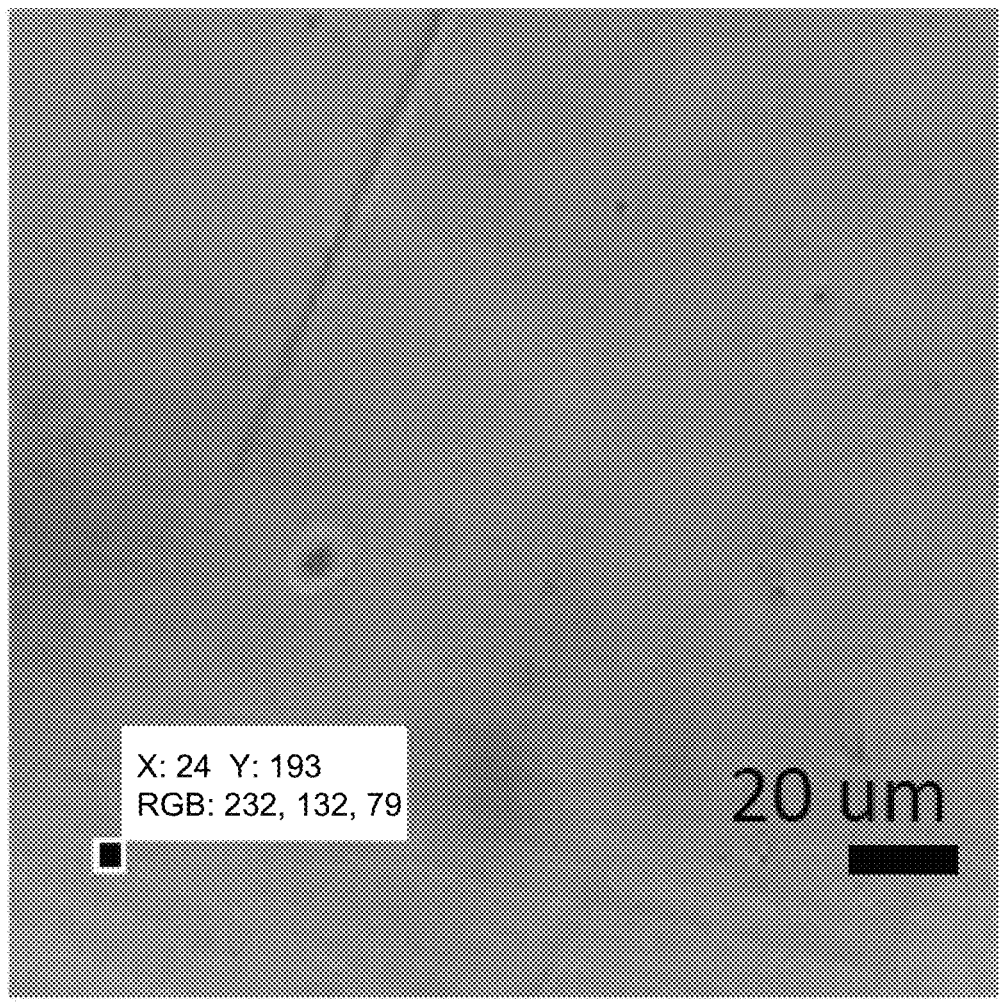
FIG. 7 illustrates an image of the LSPR active surface taken after a reaction has taken place, in accordance with embodiments.

The algorithm may select a random pixel coordinate in an image frame for analysis. The pixel may comprise a region of interest. Each pixel in an RGB image may be described by indicating a corresponding red, green, and blue value. FIG. 7 illustrates an image of the LSPR active surface taken after a reaction has taken place, in accordance with embodiments. A random pixel at coordinates (x: 24, y: 193) shows RGB values of 232, 132, and 79. A random pixel at coordinates (x: 24, y: 193) for an image of the LSPR active surface taken before the reaction has taken place may have shown different RGB values. The random pixel at coordinates (x: 24, y: 193) for the image taken before and after the reaction has taken place may comprise corresponding regions of interest. Each pixel in a greyscale image may be described by intensity information. The RGB image may contain more information than a greyscale image. The algorithm may convert an RGB image into a greyscale image by measuring the intensity of light at each pixel in a single band of the electromagnetic spectrum. Changes in intensity above a certain wavelength may be measured using filters. For example, the change in intensity may be measured using a longpass, shortpass, or bandpass filters. The random pixel coordinate (e.g., region of interest) may be analyzed for determination of intensity (e.g., for greyscale images) or RGB values (or changes in intensity/RGB values) over a series of two or more time-lapse images. Alternatively, a local area around the random pixel coordinate may be analyzed for a determination of intensity or RGB values (or changes in intensity/RGB values) over a series of two or more time-lapse images. The local area around the pixel may comprise a grid of pixels centered on or overlapping the random pixel coordinate. For example, the local area may be a 3×3, 4×4, 5×5, 6×6, 7×7, 8×8, 9×9, 10×10, 15×15, 25×25, 50×50, 100×100, or more grid of pixels centered on or overlapping the random pixel coordinate. The local area may comprise a region of interest. The same coordinates corresponding to the randomly selected pixel or same local area around the coordinates of the randomly selected pixel may be analyzed for changes within a series of images captured by the optical system. The series of images may be analyzed for changes in the corresponding regions of interest. The region of interest may correspond to an area of the LSPR sensor surface of about or less than 100 um$^2$, 50 um$^2$, 25 um$^2$, 10 um$^2$, 5 um$^2$, 4 um$^2$, 3 um$^2$, 2 um$^2$, 1 um$^2$, 0.5 um$^2$, or 0.25 um$^2$.

Alternatively, each image in the series of images may be divided into a plurality of regions of interests. The regions of interest may be a pixel, or a grid of pixels as mentioned herein. The algorithm may select one or more corresponding regions of interest and measure a change in RGB and/or greyscale intensity values over the series of images within the selected regions of interest.

The series of images may be compared based on the analysis mentioned herein. The comparison may determine if there are statistically significant differences between the corresponding regions of interest within the series of images. A comparison may involve comparing RGB or intensity values of the region of interest before and after a reaction (e.g., ELISA reaction). A comparison may involve comparing RGB or intensity values of the region of interest before, during, and after a reaction. A comparison may involve determining a change over the series of images. For example, A change in RGB values may be determined according to the formula $D = \sqrt{(\Delta R)^2 + (\Delta G)^2 + (\Delta B)^2}$ where $\Delta x$ is the change in the value of the x component, x=R, G, B. Alternatively, a change in single component of the RGB values may be determined (e.g., D=ΔR, where ΔR is the change in value of the red channel). A change in intensity may be determined according to the formula D=ΔI, where ΔI is the change in value of the intensity for the randomly selected pixel over a series of images. The change may be analyzed by comparing images taken before and after the plasmon-plasmon coupling or the ELISA reaction (e.g., binding of the analyte) on the LSPR active surface. The change may be analyzed by comparing images taken before, during, and after the plasmon-plasmon coupling or the ELISA reaction (e.g., binding of the analyte) on the LSPR active surface. A small change (e.g., on average less than one photon count) for a given pixel or local area around the pixel may be statistically significant if the change is observed for multiple sets of images. The aforementioned process may occur for a plurality of regions of interest such that a sufficient number of corresponding regions of interests have been analyzed. Thus, multiple or a plurality of regions of interest (e.g., within a single image) may be considered, simultaneously or sequentially. For example, about or more than 5, 10, 20, 50, 100, 200, 500, 1000, 1500, 2000, 3000, 4000, 5000, 7500, or 10000 regions of interest may be considered.

Figures 13, 14:
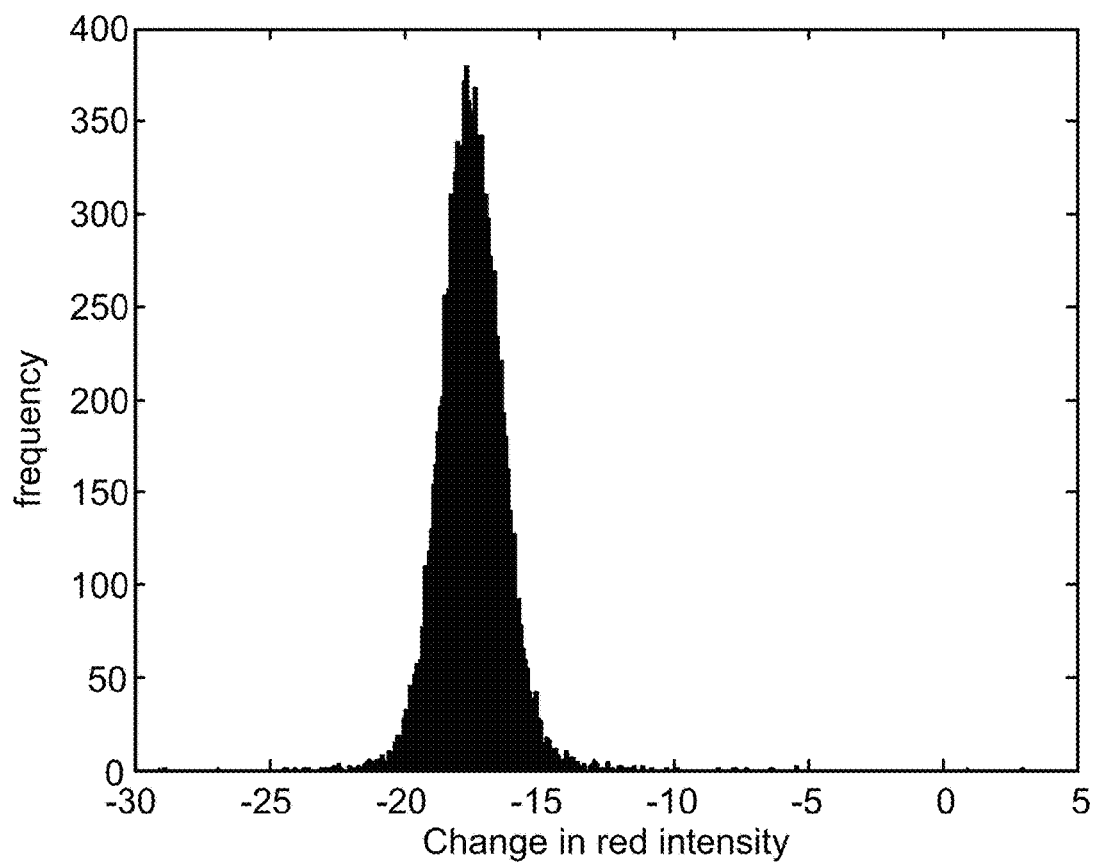
FIG. 13 is a table listing a comparison between traditional LSPR (e.g., spectroscopic detection) and digital LSPR (imaging), in accordance with embodiments.
FIG. 14 illustrates a histogram corresponding to the image of FIG. 7 that shows the relative difference in red value between before and after images on an 8 bit scale (r value between 0 to 255).

FIG. 14 illustrates a histogram of changes in red intensity values measured between two images (e.g., before and after a reaction) for a plurality of corresponding regions of interest. The histogram shows the relative difference in red value between the two images on a 8 bit scale, with red intensity values ranging from 0 to 255. A change in RGB value or change in greyscale value of 1-3 for a given pixel (or local area around the pixel) may correspond to a local spectrometric shift of about 5 nm. The algorithm may further determine a moment for the distribution of changes in RGB or greyscale intensity values. The first moment may provide an average value, while the second moment may provide a width of the distribution. In general, higher order moments may indicate higher order symmetries of the distribution and may contain valuable information. The combination of LSPR active surfaces with imaging systems mentioned herein may enable algorithms to detect and analyze analytes and samples with greater sensitivity and efficiency in cases where a photon count may be limited.

Figure 8:
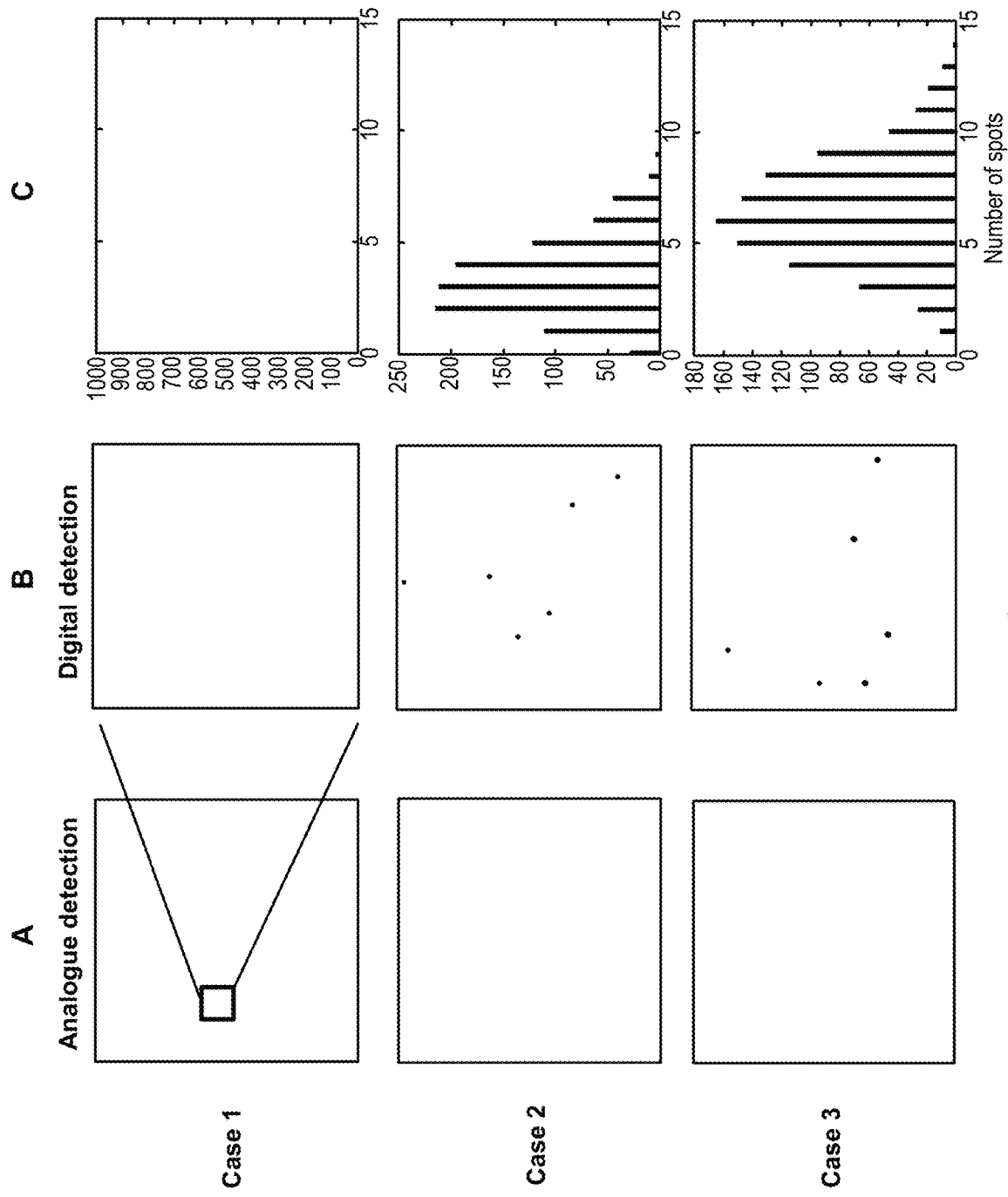
FIG. 8 illustrates a comparison of the digital LSPR concept and its superiority over traditional LSPR assay formats in terms of limit of detection with the aid of histograms, in accordance with embodiments.

The algorithm may further generate a histogram based on the RGB and/or intensity values or changes in RGB and/or intensity values that were determined over the series of images. The histogram may provide information on the presence of an analyte in a sample. FIG. 8 illustrates a comparison of the digital LSPR concept and its superiority over traditional LSPR assay formats in terms of limit of detection with the aid of histograms, in accordance with embodiments. For case 1, 2, and 3 shown, the number of marker (analyte) molecules immobilized on the sensor surface is below the level of detection for conventional spectral analysis. This is illustrated in column A, where an analogue signal (e.g., the color of the surface) does not allow differentiation between the three cases. Column B shows an image of a subsection of the LSPR active sensor surface. Faint spots of different color can be clearly discerned in cases 2 and 3, but not in case 1. If a number of spots for several randomly selected pixels (or local area around the pixels) of the entire image is analyzed and plotted in a histogram (e.g., with x-axis corresponding to a number of spots and y-axis corresponding to a change in RGB value), there is a clear distinction between the 3 cases.

The algorithm may determine a limit of detection (LOD). For example, a histogram of a reading before a reaction (e.g., a control histogram) may be compared to a histogram of a reading after reaction for various known quantities or concentrations of analytes. If there are statistically significant differences, the algorithm may determine that the analyte is present. The known quantity or concentration of analyte at which the algorithm cannot determine a statistically significant difference may be the limit of detection. For a digital detection scheme utilizing LSPR-active surfaces described herein, surface coverages (where surface coverage is defined by the ratio of occupied binding sites to total number of potential available binding sites, see example 2) as low or lower than $10^{-6}$ can be detected. This translates into detection of analyte concentrations in the (sub-) fg/mL under certain assumptions (e.g., as calculated using a Langmuir binding isotherm model and assuming a binding affinity of 1 nM). Further optimization of assay parameters, e.g. optimization of the density of primary binding components on the sensor surface, sample incubation times, etc., and of detection parameters, e.g. the intensity and/or wavelength of light used to illuminate the sensor surface, the choice of low noise detector, etc., may push the achievable detection limits much lower than sub-fg/ml. In some embodiment, the limit of detection may be better than 1 mg/ml, 100 ug/ml, 10 ug/ml, 1 ug/ml, 100 ng/ml, 10 ng/ml, 1 ng/ml, 100 pg/ml, 10 pg/ml, 1 pg/ml, 100 fg/ml, 10 fg/ml, 1 fg/ml, or 0.1 fg/ml. Thus, the systems and methods disclosed herein may detect analytes present in a sample in an amount about or less than 100 mg/ml, 10 mg/ml, 1 mg/ml, 100 ug/ml, 10 ug/ml, 1 ug/ml, 100 ng/ml, 10 ng/ml, 1 ng/ml, 100 pg/ml, 10 pg/ml, 1 pg/ml, 100 fg/ml, 10 fg/ml, 1 fg/ml, or 0.1 fg/ml.

Devices for point-of-care diagnostics (e.g. clinical diagnostics) may require sensitivities that are about or better than 200 ng/mL, 100 ng/mL, 1 ng/mL, 100 pg/mL, 10 pg/mL, or 1 pg/mL. For example, point-of-care diagnostics may require capabilities to detect analytes that are present in an amount less than 1 pg/mL in a sample. The systems and methods disclosed herein may enable miniaturized devices for high sensitivity, and point-of-care diagnostics. For example, the combination of the high density of nanostructures on the sensor surface (e.g., for measuring light reflectance), and the sensitivity enhancing labels (e.g., enzyme, metallic nanoparticles, etc), and a digital detection scheme as mentioned herein may enable sensitivities required for clinical diagnostic applications. The integration times required for capturing images to be analyzed in the systems and methods disclosed herein may about or less than 1 ms, 5 ms, 10 ms, 20 ms, 30 ms, 40 ms, 50 ms, 100 ms, or 200 ms.

The algorithm may determine a concentration of the analyte in a sample. Several known concentrations of the analyte and a corresponding signal that they generate may be measured and used for the generation of a calibration curve. An analyte may be detected as described herein, and the signal subsequently measured may be compared to a calibration curve to determine a concentration of the analyte in a sample.

The methods, devices, and systems of the present disclosure may utilize a fluidic system that is fully or partially integrated with one or more LSPR sensors. The fluidic system may be configured to deliver a sample with the analyte and/or assay reagents to the sensor surface. The fluidic system may contain pumps, valves, fluidic channels, membranes, flow cells, reaction wells or chambers, and/or reservoirs with reagents necessary for carrying out the assay. In some embodiments, all or a portion of the fluidic system components may be integrated with the LSPR sensor to create LSPR sensor chips or devices. In some embodiments, all or a portion of the fluidic system components may reside in an external housing or instrument with which the LSPR sensor chip or device interfaces.

In some embodiments, the fluidic system may include one or more fluid actuation mechanisms. Examples of suitable fluid actuation mechanisms for use in the disclosed methods, devices, and systems include application of positive or negative pressure to one or more reaction wells or reagent reservoirs, electrokinetic forces, electrowetting forces, and the like. Positive or negative pressure may be applied directly, e.g. through the use of mechanical actuators or pistons that are coupled to the reservoirs to actuate flow of the reagents from the reservoirs, through the fluidic channels and onto the sensor surface. In some embodiments, the mechanical actuators or pistons may exert force on a flexible membrane that is used to seal the reservoirs. In some embodiments, positive or negative pressure may be applied indirectly, e.g. through the use of a pressurized gas lines or vacuum lines connected with one or more reservoirs. In some embodiment, pumps may be used to drive fluid flow. These may be pumps located in a housing or instrument with which an LSPR sensor chip interfaces, or in some embodiments they may be microfabricated pumps integrated with the sensor chip.

In some embodiments, the fluidic system may include one or more valves for switching fluid flow between reservoirs and channels. These may be valves located in a housing or instrument with which an LSPR sensor chip interfaces, or in some embodiments they may be microfabricated valves integrated with the sensor chip.

The LSPR sensor chips disclosed herein may have one or more reaction wells containing an LSPR sensor where an assay takes place. The combination of fluid actuation mechanisms and control components, e.g. pumps and valves, used in the fluidic system allows fluids from the different reservoirs to be introduced into the reaction wells in the sequence required to perform a specific assay. The fluidic system may introduce the fluids from the different reservoirs in any order, either consecutively (e.g., sequentially), or simultaneously. For example, for assays utilizing secondary antibody conjugates, after the sample is introduced into the reaction wells, a diluent from a diluent reservoir may be introduced in order to rinse the reaction wells. Afterwards, secondary antibody conjugates can be introduced into the reaction wells from the secondary antibody conjugate reservoir. Next, diluent can again be introduced in order to rinse the reaction wells. Next, a reagent, such as an enzyme substrate that is enzymatically converted to an insoluble precipitate, can be introduced into the reaction wells from the reagent reservoir. Thus, LSPR sensor chips that utilize secondary antibody conjugates may contain a sample reservoir (or the sample may be deposited directly in the reaction well without a sample reservoir; additionally the sample reservoir may include diluent to be mixed with the sample), a diluent reservoir, a secondary conjugated antibody reservoir, a reagent reservoir, and a waste reservoir. Conjugated secondary antibodies may include antibodies, or antibody fragments, conjugated with any of a variety of labels or tags, including, but not limited to, enzymes, magnetic beads, metallic beads, colloids, or nanoparticles, glass beads, mass tags, and the like. In some embodiments, single step assays may be performed wherein the sample is mixed with primary and/or conjugated secondary antibodies in a single reaction mixture and contacted directly with a modified or unmodified sensor surface.

In some embodiments, the LSPR sensor chip may have a plurality of reaction wells, wherein each reaction well contains a sensor. In some embodiments, the LSPR sensor chips may have a single reaction well containing an array of sensors. The LSPR sensors may be multi-paneled or multiplexed, such that a different type of assay may be run in each reaction well. Thus, different reaction wells may contain different antibodies, DNA for running DNA assays, RNA, bacteria, and so forth that are immobilized in the reaction wells. In some embodiments, the LSPR sensor may have multiple primary antibodies or other primary binding components immobilized on a single sensor surface. The LSPR sensor chip may detect and/or quantify more than one analyte concurrently.

In some embodiments, the LSPR sensor chip may include one or more sample or reagent reservoirs. The LSPR sensor chip may detect and/or quantify more than one analyte in more than one sample concurrently. The reagents in the reservoirs may be introduced onto the sensor surface through the fluidic channels. The reservoirs may contain samples, reagents, diluents, conjugated antibodies, particles or beads, and/or waste products resulting from running an assay. For example, the LSPR sensor chip may contain one or more reservoirs for storing diluent, one or more reservoirs for storing antibody conjugates, one or more reservoirs for storing buffers or other assay reagents, and/or one or more reservoirs for storing beads. The bead reservoir may contain magnetic beads, noble metal beads, core shell beads, plasmonic colloids, and/or glass beads. Further, the LSPR sensor chip may also contain one or more waste reservoirs. In some embodiments, the reservoirs may be around 0.1 mm deep and about 10 mm in diameter, or of dimensions such that the volume is between 1 nL and 3 mL.

In some embodiments, there may be a membrane that serves as a filter placed on top of the reaction wells or sample reservoirs. In some embodiments, the sample to be assayed may be deposited onto the LSPR sensor surface by depositing the sample directly over the reaction well on top of the filter. The filter may be designed to filter out unwanted particles according to size. For example, the filter may contain appropriately sized pores that only allow smaller sized particles to filter through to the reaction wells. Unwanted particles may include cells, salt crystals, insoluble precipitates, or other particulates which may interfere with the assay or clog the fluid channels. A sample may contain one or more molecules of interest which may be separated by the membrane. Thus, different types of molecules may filter through to different reaction wells and membranes of different porosity may enable the concurrent analysis of more than one analyte in a sample. In some embodiments, the sample is introduced by depositing it over a reservoir instead of or in addition to a reaction well. The LSPR sensor may contain one or more reservoirs especially adapted to receive samples. The sample reservoirs may or may not include membranes placed on top of the reservoirs depending on whether or not filtering is desired.

In general, the reaction wells, sample and reagent reservoirs, and fluidic channels may be fabricated using any of a variety of materials, including, but not limited to glass, fused-silica, silicon, polycarbonate, polymethylmethacrylate, cyclic olefin copolymer (COC) or cyclic olefin polymer (COP), polydimethylsiloxane (PDMS), or other elastomeric materials. Suitable fabrication techniques include (depending on the choice of material), but are not limited to CNC machining, photolithography and etching, laser photoablation, injection molding, hot embossing, die cutting, and the like.

The size and shape of the fluidic channels, as well as the pressure applied to the one or more reaction wells or reservoirs, may be designed such that flow into the reaction

EXAMPLES

Example 1

Red Channel Changes in Response to a Bulk Refractive Index Change

Figure 11:
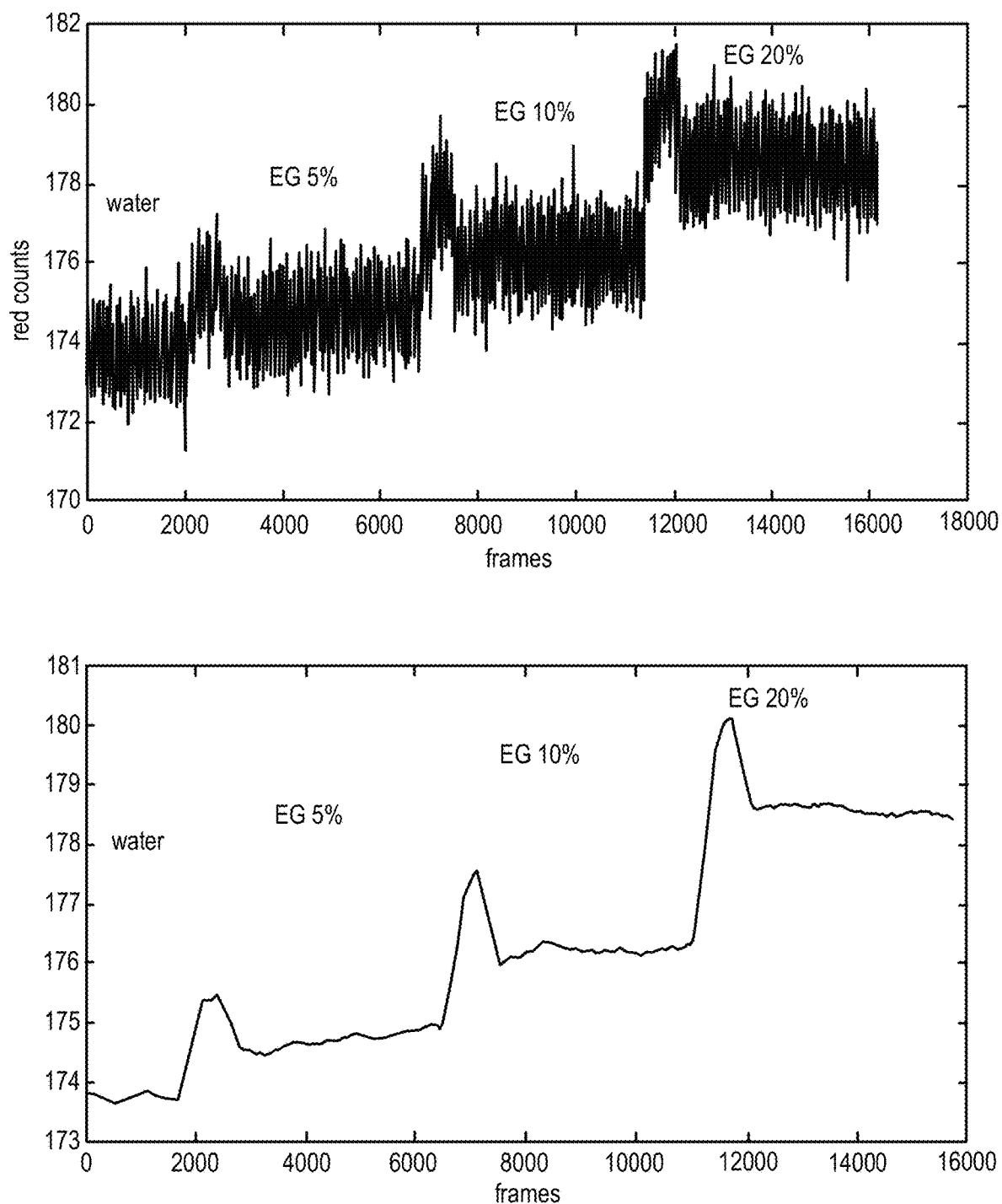
FIG. 11 illustrates changes in red channel values corresponding to various bulk index of refraction changes, in accordance with embodiments.

LSPR sensors were imaged using a ThorLabs CMOS camera (DCC1645C-HQ) with a 10× magnification objective placed ~7 mm from the surface (and ~3-4 mm from the top of a flow cell cover). In the flow cell, different solutions were pumped successively (water, 5% EG, 10% EG, and 20% EG). For each solution, a series of images were acquired and analyzed. For each series of images, pixels were selected at random and 3×3 pixels centered on the randomly selected pixel were analyzed for changes in red channel values. The sensor surface raw data collected from a color CMOS sensor shows how the red channel changes for 3×3 pixels subsection of the entire image when the bulk refractive index is successively changed from water to 5% Ethylene Glycol (EG), 10% EG, and 20% EG (shown in FIG. 11). Panel A shows a raw signal for one randomly selected pixel, while panel B shows the same signal run through an averaging filter to remove the short-time random fluctuations. The spikes correspond to perturbation when the new ethylene solution is added. The plateaus after the spikes correspond to the equilibrium value for the solution.

Figure 12:
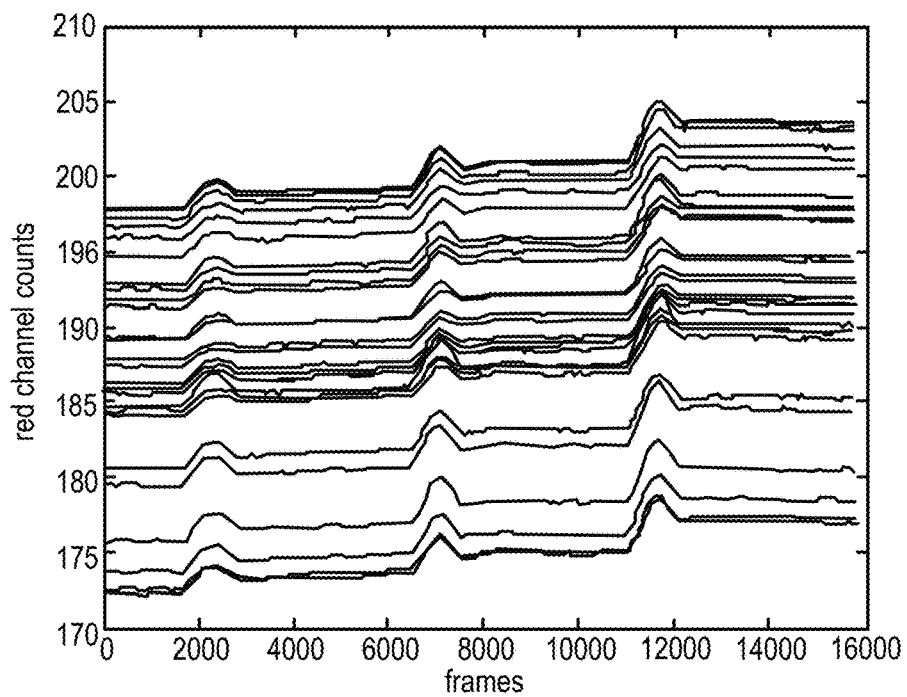
FIG. 12 illustrates changes in red channel values corresponding to various bulk index of refraction changes, in accordance with embodiments.
Figure 12:
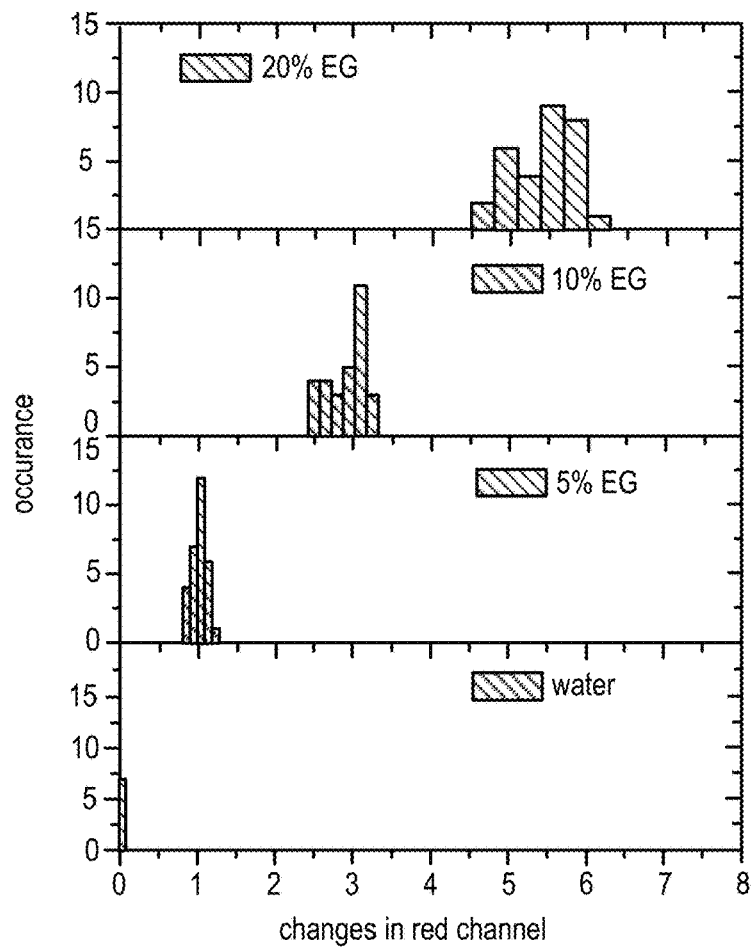

Randomly selected pixels on the images respond to the change in solution as shown in FIG. 12. To see this point, a histogram was generated based on the analyzed data for multiple pixels. Changes in red channel values were plotted on the x-axis and the number of occurrence over the whole image for the corresponding changes in red channel value were plotted on the y-axis. Changes in red channel values were clearly distinguishable as seen in FIG. 12, right. Changes of less than 1 count on average out of 255 are detectable as can be clearly seen from the histogram of 5% EG. In fact, sub-unit pixel changes can be detected by this method, because the method relies on a statistical analysis of multiple pixels of an image.

Concurrently, spectroscopic detection was performed by inserting a 50/50 beamsplitter in the detection path. One part was sent to the CMOS camera, while the other part was sent to a 2048 pixel spectrometer (AvaSpec from Avantes). The entire spectrum from ~460 nm to 720 nm was recorded and analyzed. Values obtained by the digital detection (imaging) and spectroscopic detection (traditional methods) was compared as shown by FIG. 13.

Example 2

Figure 9:
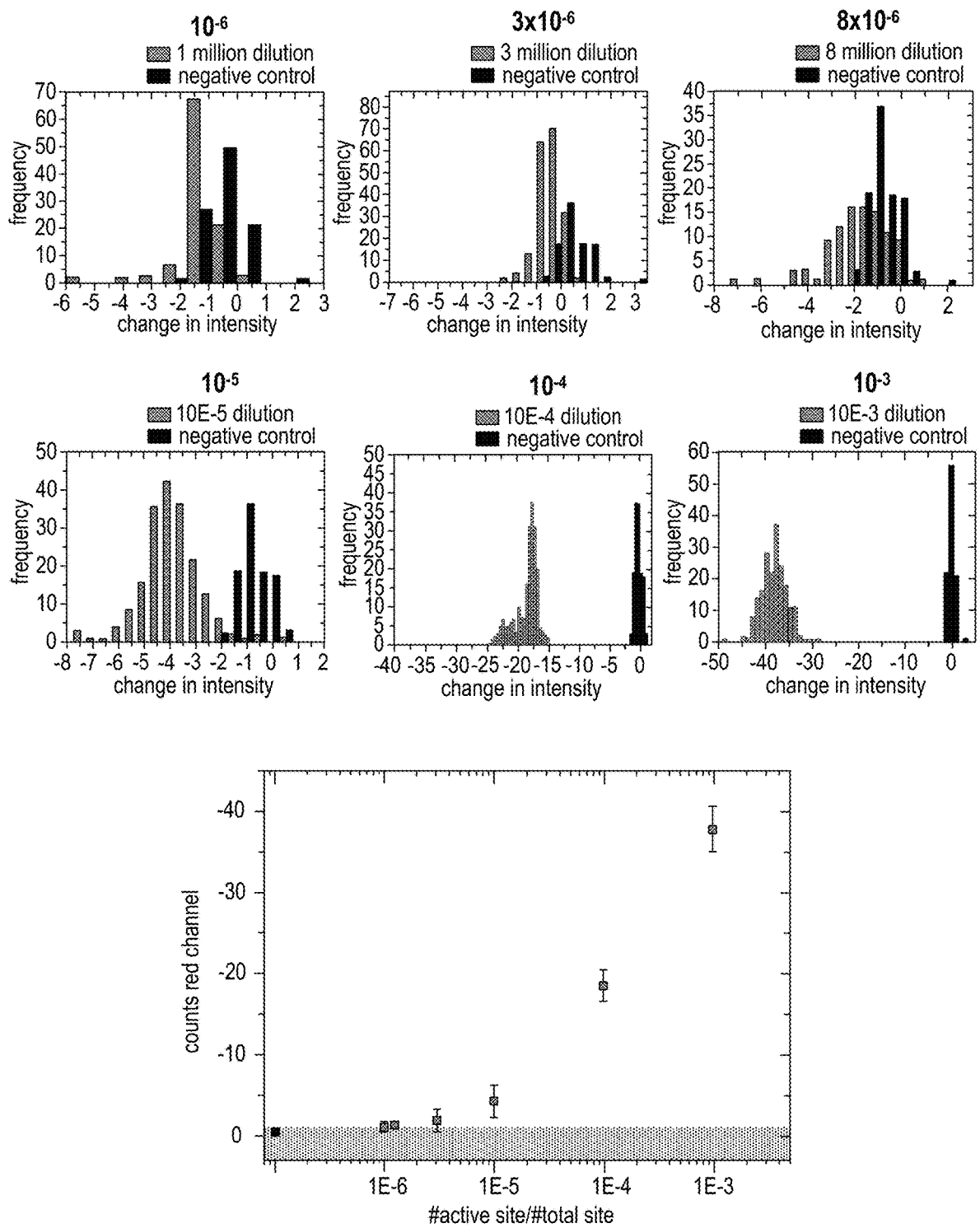
FIG. 9 illustrates the detection of analytes at several surface coverages using digital LSPR, in accordance with embodiments.

Limit of Detection Determination Based on Detection of Analytes at Various Surface Coverage FIG. 9 illustrates the detection of analytes at several surface coverages using digital LSPR, in accordance with embodiments. In a proof of concept experiment, a surface was prepared by co-adsorbing biotinylated IgG and native IgG at various ratios, but at a fixed total antibody concentration of 1 mg/mL (biotinylated IgG plus native IgG). Ratios of $10^{-6}$, $3*10^{-6}$, $8*10^{-6}$, $10^{-5}$, $10^{-4}$, and $10^{-3}$ were specifically prepared. The total concentration was large enough to saturate the surface. The surface coverage in biotinylated IgG was assumed to correspond to the ratio of biotinylated IgG to total antibody. Hence a surface coverage of $10^{-6}$ meant that during co-adsorption of biotinylated IgG and native IgG there were 1 biotinylated IgG per $10^6$ native IgG. These model surfaces mimic the coverage of antigen in real assays. The biotinylated antibodies on the LSPR surface was detected using streptavidin-alkaline phosphatase amplification scheme followed by BCIP/NBT color development. Images of the same area before and after the addition of the BCIP/NBT was collected in PBS. The RGB values of randomly selected regions of interest was analyzed and changes in the value of the Red component of the color image was histogramed. For each concentration, the histogram plotted in black corresponds to the reading before the reaction, while the histogram plotted in grey corresponds to the measured value after the enzymatic reaction. Histograms plotted in black were compared to histograms plotted in grey for multiple surface coverages. FIG. 9 demonstrates that surface coverages (where surface coverage is defined by the ratio of occupied binding sites to total number of potential available binding sites) as low as $10^{-6}$ can be detected, since the histogram distributions show a statistically significant difference in their first (average) and second moment (width) values.

Figure 10:
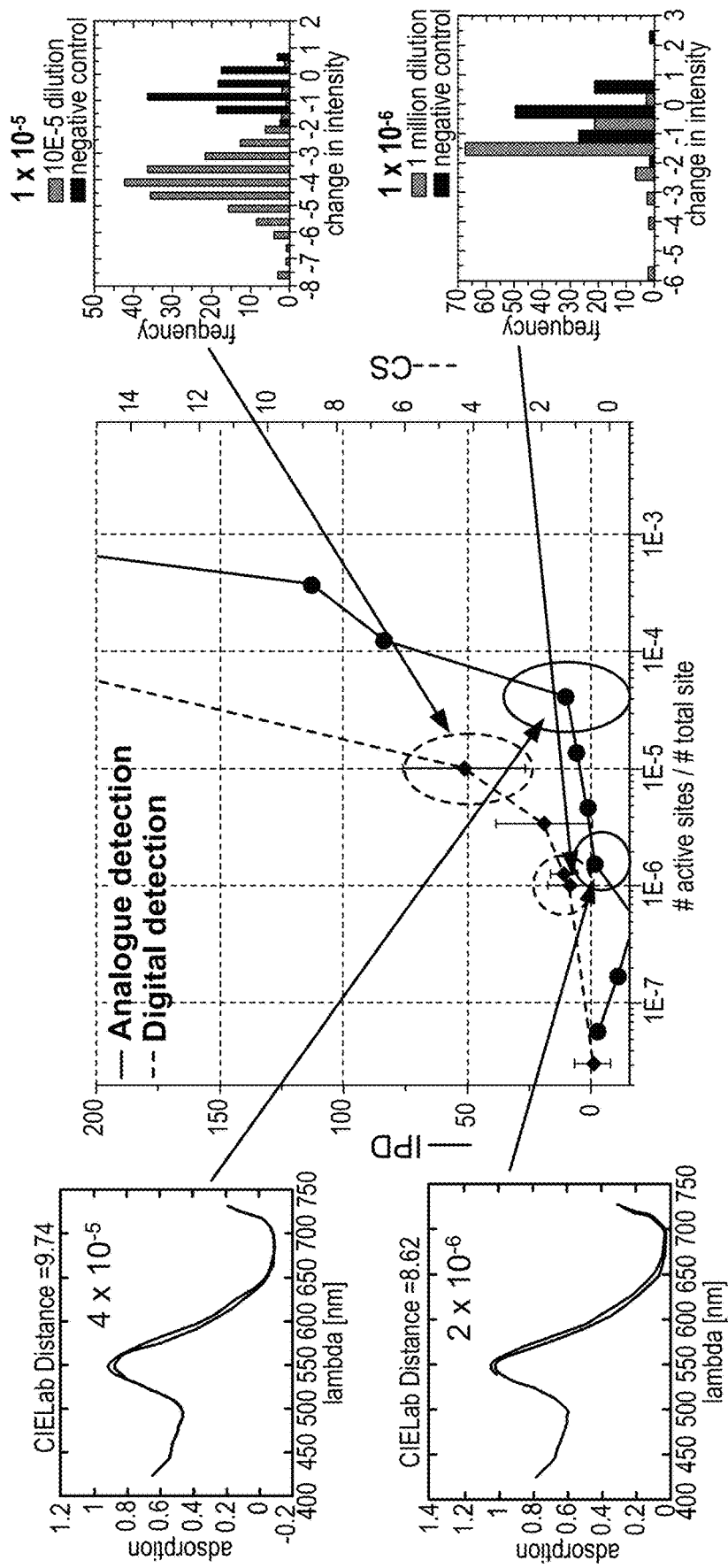
FIG. 10 illustrates a comparison between traditional LSPR and digital LSPR at several surface coverages, in accordance with embodiments.

Spectroscopic detection (analogue detection) was performed in conjunction with the digital detection. Comparison of an assay for detection of biotinylated IgG on model surfaces at several surface coverages (i.e. number of biotinylated IgG vs native IgG on a saturated surface) from $10^{-3}$ to $10^{-7}$. The analogue detection reached a LOD between surface coverage of $10^{-4}$ and $4*10^{-5}$ s shown by FIG. 10. In fact, the spectra for the surfaces with $4*10^{-5}$ coverage before and after the reaction were barely distinguishable and at coverage of $2\times10^{-6}$ were mostly overlay. In contrast, the digital reading for surface coverage of $10^{-5}$ and $10^{-6}$ clearly showed a readout difference before and after the reaction.

Example 3 (Prophetic)

Detection of Nucleic Acid Target Molecules

In some embodiments, the disclosed digital LSPR methods and systems may be used for detection of target nucleic acid sequences in biological or environmental samples. One of skill in the art can envision immobilizing capture probes on the LSPR sensor surface that are complementary to a portion of one or more target nucleic acid sequences. Immobilization of probes on the surface may be accomplished by any of a variety of techniques known to those of skill in the art, for example by using patterned, self-assembled monolayers of thiolated oligonucleotides (or suitable linker molecules, as necessary) on noble metal surfaces. The surface may then be contacted with a sample of interest under conditions that promote hybridization of complementary sequences such that target nucleic acid molecules, if present, are captured and immobilized on the sensor surface. The sensor surface may then be rinsed and contacted with a solution comprising detection probes that are complementary to a portion of the distal end of the one or more immobilized targets. The detection probes are incubated with the LSPR sensor surface under conditions that promote hybridization of the detection probes to the immobilized targets, if present, after which the sensor surface may be rinsed to remove any non-hybridized detection probe molecules.

In some embodiments, the detection probes may be labeled with a sensitivity enhancement label such as an enzyme that catalyzes the conversion of a reactant to an insoluble product, as discussed above, thereby resulting in local refractive index changes that may be detected using the digital imaging techniques disclosed herein. In some embodiments, the detection probes may be labeled with metal nanoparticles, as discussed above, which induce localized plasmon-plasmon coupling that may be detected using the digital imaging techniques disclosed herein. In some embodiments, for example when two or more target nucleic acid molecules are to be detected, the capture probes may be immobilized in specific spatial patterns on the sensor surface so that detection of the two or more target molecules may be distinguished from one another. In some embodiments, the detection probes may be labeled with two or more different sensitivity enhancement labels that produce distinguishable changes in the optical properties of the LSPR sensor surface such that detection of two or more target molecules may be distinguished from one another.

In general, the capture and detection probes will comprise oligonucleotide probes of between about 20 and about 40 nucleotides in length. In some embodiments, the lengths of the capture and/or detection probes may be either shorter or longer than this, for example, probes may be 10 nucleotides in length, or 50 nucleotides in length. In general, one of the design objectives for the design of capture and detection probes will be to optimize the stability and specificity of the hybridized probe-target sequences. In some embodiments, the length of the capture and/or detection probes may be adjusted depending on the length of the target nucleotide sequence in order to bring the sensitivity enhancement label of the detection probe into as close proximity with the LSPR sensor surface as possible. In some embodiments, the capture and detection probes may be designed such that the sensitivity enhancement label of the hybridized detection probe is kept in close proximity to the LSPR sensor surface regardless of the length of the target nucleic acid sequence, for example, by designing the detection probes such that they hybridize to sections of the immobilized target sequences that are in close proximity to those which hybridize to the capture probes.

Examples of potential applications for this approach include, but are not limited to, detection of specific gene sequences or fragments thereof, detection of specific mRNA or microRNA sequences, and the like.

Example 4 (Prophetic)

Nucleic Acid Sequencing

In some embodiments, the disclosed digital LSPR methods and systems may be used for sequencing of nucleic acid molecules using, for example, a sequencing-by-synthesis approach. Template molecules to be sequenced may be immobilized on the sensor surface using any of a variety of techniques known to those of skill in the art, for example, by hybridization to, or ligation with, universal adaptor oligonucleotides immobilized on the sensor surface. In some embodiments, the adaptor oligonucleotides may comprise forward and reverse primer sequences, and solid-phase amplification techniques (e.g. bridge amplification) may be used to create spatially separated template molecule clusters. A universal sequencing primer is then hybridized with the template molecules to initiate the sequencing reaction. Polymerase and labeled dNTPs (e.g. where the dNTPs are labeled with metal nanoparticles that induce plasmon-plasmon coupling with the LSPR sensor surface) are then contacted with the sensor surface in a step-wise fashion (i.e. using one labeled dNTP per cycle), and the optical properties of the sensor surface are monitored using the digital imaging techniques described above to determine whether or not a base has been added in a given polymerase reaction step. In some embodiments, the change in signal may be monitored in the presence of the cumulative "background" signal arising from successive addition of labeled nucleotides. In some embodiments, the dNTPs may be labeled with metal nanoparticles using cleavable attachment chemistries such that the nanoparticle labels may be removed from the growing oligonucleotide strands between each polymerase reaction, thereby minimizing the accumulation of "background signal" and improving the sensitivity to single base additions. In some embodiments, high throughput may be achieved by simultaneously monitoring the reactions occurring at the location of many immobilized template molecules (or template molecule clusters) simultaneously with the use of the digital imaging techniques disclosed herein. In some embodiments, the potential read-length that can be achieved may be impacted by the distance-dependence for efficient plasmon-plasmon coupling.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A computer-implemented method, comprising:
   randomly selecting a plurality of corresponding regions of interest in each of a series of two or more images of a nanostructured sensor surface, wherein the nanostructured sensor surface is capable of sustaining a localized surface plasmon resonance;
   measuring a change in RGB value or greyscale value for each of the plurality of corresponding regions by comparing the RGB value or greyscale value for corresponding regions of interest in different images of the series of two or more images; and
   determining a presence of an analyte based on analyzing the measured changes in RGB value or greyscale value for the plurality of corresponding regions.

2. The method of claim 1, wherein a limit of detection for determining the presence of the analyte is determined to be better than 1 ng/mL based on analyzing a control reading and one or more readings corresponding to one or more known quantities or concentrations of the analyte.

3. The method of claim 1, wherein a limit of detection for determining the presence of the analyte is determined to be better than 1 pg/mL based on analyzing a control reading and one or more readings corresponding to one or more known quantities or concentrations of the analyte.

4. The method of claim 1, further comprising determining a concentration of the analyte based on the measured changes in RGB value or greyscale value.

5. The method of claim 1, wherein the measured change in RGB value or greyscale value is a change in RGB value or greyscale value of light reflected from the nanostructured sensor surface.

6. The method of claim 1, wherein the series of two or more images are captured before and after a local analyte-induced change occurs.

7. The method of claim 1, wherein the nanostructured sensor surface is contacted with a primary binding component, the analyte, and a secondary binding component sequentially or simultaneously, wherein the secondary binding component is a sensitivity enhancing label.

8. The method of claim 7, wherein the sensitivity enhancing label is an enzyme that catalyzes a conversion of a reactant to an insoluble product, or a metallic nanoparticle that is capable of inducing plasmon-plasmon coupling between the metallic nanoparticle and the nanostructured sensor surface.

9. The method of claim 1, wherein the analyte is present in a sample an amount of 100 ng/mL or less.

10. The method of claim 1, wherein the analyte is present in a sample in an amount of 1 pg/mL or less.

11. The method of claim 1, further comprising receiving a report comprising a result of the method and making a healthcare decision based on the reported result, wherein the sample is a patient sample.

12. The method of claim 1, wherein the nanostructured sensor surface comprises a continuous nanostructured metallic thin film across a sensor substrate.

13. The method of claim 1, wherein determining the presence of the analyte comprises:
   analyzing measured changes in RGB value and intensity of light for the plurality of corresponding regions.

14. The method of claim 13, wherein the measured changes in RGB value and intensity of light for the plurality of corresponding regions are based on comparing the RGB value and intensity of light for corresponding regions of interest in different images of the series of two or more images.

15. The method of claim 1, further comprising:
   generating a histogram relating to the measured changes in RGB value or greyscale value for the plurality of corresponding regions, wherein the determining the presence of the analyte is based on the histogram.

16. The method of claim 1, wherein analyzing the measured changes in RGB value or greyscale value for the plurality of corresponding regions comprises:
   identifying one or more statistically significant differences in the measured changes in RGB value or greyscale value.

17. The method of claim 1, wherein the nanostructured sensor surface comprises: a first metallic thin film layer, a second metallic thin film layer, and a dielectric layer at least partially between the first metallic thin film layer and the second metallic thin film layer.

18. The method of claim 1, wherein the nanostructured sensor surface comprises: a first plurality of metallic thin film layers, a second plurality of metallic thin film layers, and a dielectric layer at least partially between the first plurality of metallic thin film layers and the second plurality of metallic thin film layers.

* * * * *

UNITED STATES PATENT AND TRADEMARK OFFICE
CERTIFICATE OF CORRECTION

PATENT NO. : 10,928,319 B2
APPLICATION NO. : 16/007559
DATED : February 23, 2021
INVENTOR(S) : Daniele Gerion et al.

It is certified that error appears in the above-identified patent and that said Letters Patent is hereby corrected as shown below:

On the Title Page

On the page 2, in Column 2, under "Other Publications", Line 2, delete "extrememly" and insert -- extremely --, therefor.

On the page 2, in Column 2, under "Other Publications", Line 8, delete "Nanomater" and insert -- Nanometer --, therefor.

In the Drawings

On sheet 9 of 10, in Figure 12, Line 17, delete "occurance" and insert -- occurrence --, therefor.

In the Specification

In Column 8, Line 45, delete "embodiments" and insert -- embodiments. --, therefor.

In Column 10, Line 41, delete "3'-indolyphosphate" and insert -- 3'-indolylphosphate --, therefor.

In Column 16, Line 33, delete "3'-indolyphosphate" and insert -- 3'-indolylphosphate --, therefor.

In Column 19, Line 43, delete "historgram" and insert -- histogram --, therefor.

In the Claims

In Column 26, Line 55, in Claim 2, delete "concentations" and insert -- concentrations --, therefor.

In Column 26, Line 60, in Claim 3, delete "concentations" and insert -- concentrations --, therefor.

In Column 27, Line 16, in Claim 9, before "an" insert -- in --.

Signed and Sealed this
Twentieth Day of April, 2021

Drew Hirshfeld
*Performing the Functions and Duties of the
Under Secretary of Commerce for Intellectual Property and
Director of the United States Patent and Trademark Office*